(12) United States Patent
Anderson et al.

(10) Patent No.: US 6,997,923 B2
(45) Date of Patent: Feb. 14, 2006

(54) METHOD AND APPARATUS FOR EMR TREATMENT

(75) Inventors: R. Rox Anderson, Lexington, MA (US); Gregory B. Altshuler, Wilmington, MA (US); Dieter Manstein, Boston, MA (US); Sergey B. Biruchinsky, Saint Petersburg (RU); Andrei V. Erofeev, North Andover, MA (US)

(73) Assignees: Palomar Medical Technologies, Inc., Burlington, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 10/033,302

(22) Filed: Dec. 27, 2001

(65) Prior Publication Data

US 2002/0161357 A1    Oct. 31, 2002

Related U.S. Application Data

(60) Provisional application No. 60/258,855, filed on Dec. 28, 2000.

(51) Int. Cl.
*A61B 18/18* (2006.01)

(52) U.S. Cl. .............................. 606/9; 606/10; 606/13; 606/17; 607/88; 607/89

(58) Field of Classification Search ................ 606/63, 606/7–13; 602/88–95
See application file for complete search history.

(56) References Cited

U.S. PATENT DOCUMENTS

| | | |
|---|---|---|
| 3,327,712 A | 6/1967 | Kaufman |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,834,391 A | 9/1974 | Block |
| 3,900,034 A | 8/1975 | Katz et al. |
| 4,233,493 A | 11/1980 | Nath |
| 4,316,467 A | 2/1982 | Muckerheide |
| 4,388,924 A | 6/1983 | Weissman et al. |
| 4,461,294 A | 7/1984 | Baron |
| 4,539,987 A | 9/1985 | Nath et al. |
| 4,608,978 A | 9/1986 | Rohr |
| 4,617,926 A | 10/1986 | Sutton |

(Continued)

FOREIGN PATENT DOCUMENTS

AT    400 305 B    4/1995

(Continued)

OTHER PUBLICATIONS

Altshuler, Grigory B., et al., "Acoustic response of hard dental tissues to pulsed laser action," *SPIE*, vol. 2080, Dental Applications of Lasers (1993), pp. 97-103.

(Continued)

*Primary Examiner*—David M. Shay
(74) *Attorney, Agent, or Firm*—Thomas J. Engellenner; Reza Mollaaghababa; Nutter McClennen & Fish LLP

(57) ABSTRACT

A method and apparatus are provided for performing a therapeutic treatment on a patient's skin by concentrating applied radiation of at least one selected wavelength at a plurality of selected, three-dimensionally located, treatment portions, which treatment portions are within non-treatment portions. The ratio of treatment portions to the total volume may vary from 0.1% to 90%, but is preferably less than 50%. Various techniques, including wavelength, may be utilized to control the depth to which radiation is concentrated and suitable optical systems may be provided to concentrate applied radiation in parallel or in series for selected combinations of one or more treatment portions.

57 Claims, 19 Drawing Sheets

U.S. PATENT DOCUMENTS

| | | | | |
|---|---|---|---|---|
| 4,653,495 A | * | 3/1987 | Nanaumi | 606/9 |
| 4,718,416 A | | 1/1988 | Nanaumi | |
| 4,733,660 A | | 3/1988 | Itzkan | |
| 4,747,660 A | | 5/1988 | Nishioka | |
| 4,819,669 A | | 4/1989 | Politzer | |
| 4,832,024 A | | 5/1989 | Boussignac | |
| 4,860,172 A | | 8/1989 | Schlager et al. | |
| 4,860,744 A | | 8/1989 | Johnson et al. | |
| 4,917,084 A | | 4/1990 | Sinofsky | |
| 4,926,227 A | | 5/1990 | Jensen | |
| 4,945,239 A | | 7/1990 | Wist et al. | |
| 5,000,752 A | * | 3/1991 | Hoskin et al. | 606/9 |
| 5,057,104 A | | 10/1991 | Chess | |
| 5,059,192 A | | 10/1991 | Zaias | |
| 5,065,515 A | | 11/1991 | Iderosa | |
| 5,071,417 A | | 12/1991 | Sinofsky | |
| 5,108,388 A | | 4/1992 | Trokel | |
| 5,137,530 A | | 8/1992 | Sand | |
| 5,140,984 A | | 8/1992 | Dew et al. | |
| 5,178,617 A | | 1/1993 | Kuizenga et al. | |
| 5,182,557 A | | 1/1993 | Lang | |
| 5,182,857 A | | 2/1993 | Simon | |
| 5,196,004 A | | 3/1993 | Sinofsky | |
| 5,207,671 A | | 5/1993 | Franken et al. | |
| 5,225,926 A | | 7/1993 | Cuomo et al. | |
| 5,226,907 A | | 7/1993 | Tankovich | |
| 5,282,797 A | | 2/1994 | Chess | |
| 5,300,097 A | | 4/1994 | Lerner et al. | |
| 5,304,170 A | * | 4/1994 | Green | 606/9 |
| 5,306,274 A | | 4/1994 | Long | |
| 5,320,618 A | | 6/1994 | Gustafsson | |
| 5,334,191 A | | 8/1994 | Poppas et al. | |
| 5,334,193 A | | 8/1994 | Nardella | |
| 5,344,418 A | | 9/1994 | Ghaffari | |
| 5,348,551 A | | 9/1994 | Spears et al. | |
| 5,350,376 A | | 9/1994 | Brown | |
| 5,380,317 A | | 1/1995 | Everett et al. | |
| 5,405,368 A | | 4/1995 | Eckhouse | |
| 5,415,654 A | | 5/1995 | Daikuzono | |
| 5,425,728 A | | 6/1995 | Tankovich | |
| 5,474,549 A | | 12/1995 | Ortiz et al. | |
| 5,486,172 A | | 1/1996 | Chess | |
| 5,505,726 A | | 4/1996 | Meserol | |
| 5,519,534 A | | 5/1996 | Smith et al. | |
| 5,578,866 A | | 11/1996 | DePoorter et al. | |
| 5,595,568 A | | 1/1997 | Anderson et al. | |
| 5,616,140 A | | 4/1997 | Prescott | |
| 5,620,478 A | | 4/1997 | Eckhouse | |
| 5,626,631 A | | 5/1997 | Eckhouse | |
| 5,630,811 A | | 5/1997 | Miller | |
| 5,649,972 A | | 7/1997 | Hochstein | |
| 5,662,644 A | | 9/1997 | Swor | |
| 5,683,380 A | | 11/1997 | Eckhouse | |
| 5,698,866 A | | 12/1997 | Doiron et al. | |
| 5,735,844 A | | 4/1998 | Anderson et al. | |
| 5,735,884 A | | 4/1998 | Thompson et al. | |
| 5,743,901 A | | 4/1998 | Grove et al. | |
| 5,755,751 A | | 5/1998 | Eckhouse | |
| 5,759,200 A | | 6/1998 | Azar | |
| 5,782,249 A | | 7/1998 | Weber et al. | |
| 5,810,801 A | | 9/1998 | Anderson et al. | |
| 5,824,023 A | | 10/1998 | Anderson | |
| 5,828,803 A | | 10/1998 | Eckhouse | |
| 5,830,208 A | | 11/1998 | Muller | |
| 5,836,999 A | | 11/1998 | Eckhouse | |
| 5,853,407 A | | 12/1998 | Miller | |
| 5,871,479 A | | 2/1999 | Furmoto et al. | |
| 5,885,211 A | * | 3/1999 | Eppstein et al. | 606/9 |
| 5,885,273 A | | 3/1999 | Eckhouse et al. | |
| 5,885,274 A | | 3/1999 | Fullmer et al. | |
| 5,944,748 A | | 8/1999 | Mager et al. | |
| 5,954,710 A | | 9/1999 | Paolini et al. | |
| 5,964,749 A | | 10/1999 | Eckhouse et al. | |
| 5,968,033 A | | 10/1999 | Fuller et al. | |
| 5,968,034 A | | 10/1999 | Fullmer et al. | |
| 6,015,404 A | | 1/2000 | Altshuler et al. | |
| 6,027,495 A | | 2/2000 | Miller | |
| RE36,634 E | | 3/2000 | Ghaffari | |
| 6,050,990 A | * | 4/2000 | Tankovich et al. | 606/9 |
| 6,056,738 A | | 5/2000 | Marchitto et al. | |
| 6,059,820 A | * | 5/2000 | Baronov | 607/89 |
| 6,074,382 A | | 6/2000 | Asah et al. | |
| 6,080,146 A | | 6/2000 | Altshuler et al. | |
| 6,096,029 A | | 8/2000 | O'Donnell, Jr. | |
| 6,096,209 A | | 8/2000 | O'Brien et al. | |
| 6,104,959 A | | 8/2000 | Spertell | |
| 6,120,497 A | | 9/2000 | Anderson | |
| 6,149,644 A | | 11/2000 | Xie | |
| 6,174,325 B1 | | 1/2001 | Eckhouse | |
| 6,197,020 B1 | | 3/2001 | O'Donnell, Jr. | |
| 6,228,075 B1 | * | 5/2001 | Furumoto | 606/9 |
| 6,273,884 B1 | | 8/2001 | Altshuler et al. | |
| 6,273,885 B1 | | 8/2001 | Koop et al. | |
| 6,280,438 B1 | | 8/2001 | Eckhouse et al. | |
| 6,439,888 B1 | | 8/2002 | Boutoussov et al. | |
| 6,475,211 B1 | | 11/2002 | Chess et al. | |
| 6,600,951 B1 | * | 7/2003 | Anderson | 606/9 |

FOREIGN PATENT DOCUMENTS

| | | |
|---|---|---|
| DE | 3837248 A | 5/1990 |
| EP | EP 0 142 671 | 5/1985 |
| EP | EP 0 565 331 | 10/1993 |
| EP | EP 0 724 894 | 8/1996 |
| EP | EP 0 726 083 | 8/1996 |
| EP | EP 0 736 308 | 10/1996 |
| EP | EP 0 755 698 | 1/1997 |
| EP | EP 0 763 371 | 3/1997 |
| EP | EP 0 765 673 | 4/1997 |
| EP | EP 0 765 674 | 4/1997 |
| EP | EP 0 783 904 A2 | 7/1997 |
| EP | 1 038 505 A | 9/2000 |
| FR | 2 591 902 | 7/1987 |
| GB | 2 044 908 A | 10/1980 |
| GB | 2 123 287 A | 1/1982 |
| GB | 2 360 946 A | 10/2001 |
| RU | 95105406 | 6/1997 |
| RU | 94012665 | 9/1997 |
| RU | 94040344 | 9/1997 |
| RU | 95102749 | 11/1997 |
| RU | 4954402 | 10/1998 |
| SU | 719439 | 8/1975 |
| SU | 741747 | 10/1977 |
| SU | 1257475 A1 | 9/1986 |
| SU | 1326962 A1 | 7/1987 |
| SU | 532304 | 9/1994 |
| WO | WO 86/02783 | 9/1986 |
| WO | WO 90/00420 | 1/1990 |
| WO | WO 92/16338 | 1/1992 |
| WO | WO 92/19165 | 12/1992 |
| WO | WO 93/05920 A1 | 1/1993 |
| WO | WO 95/15725 A1 | 6/1995 |
| WO | WO 95/32441 A1 | 11/1995 |
| WO | WO 96/23447 A1 | 8/1996 |
| WO | WO 96/25979 A1 | 8/1996 |
| WO | WO 97/13458 | 4/1997 |
| WO | WO 98/04317 | 5/1998 |
| WO | WO 98/24507 | 11/1998 |
| WO | WO 98/51235 A1 | 11/1998 |
| WO | WO 98/52481 A1 | 11/1998 |
| WO | WO 99/38569 A2 | 5/1999 |
| WO | WO 99/38569 A3 | 5/1999 |

| | | | |
|---|---|---|---|
| WO | WO 99/27997 A1 | 6/1999 |
| WO | WO 99/29243 A1 | 6/1999 |
| WO | WO 99/46005 A1 | 9/1999 |
| WO | WO 00/03257 A1 | 1/2000 |
| WO | WO 00/71045 X | 11/2000 |
| WO | WO 00/74781 A | 12/2000 |
| WO | WO 00/78242 P | 12/2000 |
| WO | WO 00/78242 X | 12/2000 |
| WO | WO 01/34048 | 5/2001 |
| WO | WO 01/03257 A1 | 11/2001 |

OTHER PUBLICATIONS

Altshuler, G. B., et al., "Extended Theory of Selective Photothermolysis," *Lasers in Surgery and Medicine*, 29:416-432 (2001).

Amy, Robert L. and Storb, R., "Selective Mitochondrial Damage by a Ruby Laser Microbeam: An Electron Micrcoscopic Study," *Science*, 15:756-758, Nov. 1965.

Anderson, R. Rox, et al., "The Optics of Human Skin," *The Journal of Investigative Dermatology*, vol. 77, No. 1, pp. 13-19, 1981.

Anderson, R. R, and Parrish, J. A., M.D., "Selective Photothermolysis: Precise Microsurgery by Selective Absorption of Pulsed Radiation," *Science*, 220:524-527, 1983.

Belikov, A. V., et al., "Identification of enamel and dentine under tooth laser treatment," *SPIE*, Progress in Biomedical Optics, Europt Series, Proceedings of Medical Applications of Lasers III, vol. 2623, pp. 109-116.

Dover, J. S., et al., "Pigmented Guinea Pig Skin Irradiated with Q-Switched Ruby Laser Pulses," *Arch Dermatol*, 125: 43-49, 1989.

Finkelstein, L. H. and Blatstein, Lee M., "Epilation of Hair-Bearing Urethral Grafts Using the Neodymium: YAG Surgical Laser," *The Journal of Urology*, 146:840-842, 1991.

Goldman, L., "Laser History and Theory," "Laser Instrumentation," and "Summer and Conclusions," Biomedical Aspects of the Laser, New York, Springer-Verlag, 1967, pp iii-11, 220-232.

Goldman, L., "Dermatologic Manifestation of Laser Radiation," *Fed Am Soc Exp Biology*, Suppl. 14:S-92-S-93, 1965.

Goldman, L., "Effects of New Laser Systems on the Skin," *Arch Dermatol*, 108:385-390, 1973.

Goldman, L., "Laser Surgery for Skin Cancer," *NY State J Med*, 77:1897-1900, 1977.

Goldman, L., "Surgery by Laser for Malignant Melanoma," *J Dermatol. Surg. Oncol.*, 5(2):141-144, 1979.

Goldman, L., "The Skin," *Arch Environ Health*, 18:434-426, 1969.

Goldman, L. and Richfield, D.F., The Effect of Repeated Exposures to Laser Beams, *Acta Derm.-Veneoral*, 44:264-268, 1964.

Goldman, L. and Rockwell, J., "Laser Action at the Cellular Level," *JAMA*, 198:641-644, 1966.

Goldman, L. and Wilson, R. G., "Treatment of Basal Cell Epithelioma by Laser Radiation," *JAMA*, 189:773-775, 1964.

Goldman, L., et al., "Biomedical Aspects of Lasers," *JAMA*, 188:230-234, 1964.

Goldman, L., et al., "Effect of the Laser Beam on the Skin: Preliminary and Short Report," *The Journal of Investigative Dermatology*, 40:121-122, 1963.

Goldman, L., et al., "Effect of the Laser Beam on the Skin III. Exposure of Cytological Preparations," *The Journal of Investigative Dermatology*, 42:247-251, 1964.

Goldman, L., et al., "Impact of the Laser on Nevi and Melanomas," *Arch Dermatol*, 90:71-75, 1964.

Goldman, L., et al., "Laser Treatment of Tatoos," *JAMA*, 210:163-166, 1967.

Goldman, L., et al., "Long-Term Laser Exposure of a Senile Freckle," *Arch Environ Health*, 22:401-403, 1971.

Goldman, L., et al., Pathology of the Effect of the Laser Beam on the Skin, *Nature*, 197:912-914, 1963.

Goldman, L., et al., "Preliminary Investigation of fat Embolization from Pulsed Ruby Laser Impacts of Bone," *Nature*, 221:361-363, 1969.

Goldman, L., et al., "Radiation from a Q-Switched Ruby Laser. Effect of Repeated Impacts of Power Output of 10 Megawatts on a Tattoo of Man," *The Journal of Investigative Dermatology*, 44:69-71, 1965.

Goldman, L., et al., "Replica Microscopy and Scanning Electron Microscopy of Lawer Impacts on the Skin," *The Journal of Investigative Dermatology*, 52:18-24, 1969.

Grossman, M.C., et al., "Damage to Hair Follicles by Normal-mode Ruby Laser Pulses," *Journal of the American Academy of Dermatology*, 35(6):889-894, 1996.

Grossman, M.C., et al., "Laser Targeted at Hair Follicles," *Lasers Med Surg.*, Suppl. 7:221, 1995.

Klein, E., et al., "Biological Effects of Laser Radiation I: Threshold Studies and Reversible Depigmentation in Rodent Skin," *Northeast Electronics Research and Engineering Meeting—NEREM Record—1965*, IEEE Catalogue No. F-60, (Nov. 4, 1965) pp. 108-109.

Kuhns, J. G., et al., "Biological Effects of Laser Radiation II: Effects of Laser Irradiation on the Skin," *Northeast Electronics Research and Engineering Meeting—NEREM Record 1965*, IEEE Catalogue No. F-60, (Nov. 4, 1965) pp. 152-153.

Kuhns, James G., et al., "Laser Injury in Skin," *Laboratory Investigation*, vol. 17, No. 1, (Jul., 1967) pp. 1-13.

Manstein, Dieter, et al., "Selective Photothermolysis of Lipid-Rich Tissue," *American Society for Laser Medicine and Surgery Abstracts*, No. 17,American Society for Laser Medicine and Surgery Twenty-First Annual Meeting, Apr. 20-22, 2001, p. 6.

Margolis, R. J., et al., "Visible Action Spectrum for Melanin-Specific Selective Photothermolysis," *Lasers in Surgery and Medicine*, 9:389-397, 1989.

Parrish, J. A., M.D., et al., "Selective Thermal Effects with Pulsed Irradiation from Lasers: From Organ to Organelle," *The Journal of Investigative Dermatology*, 80:75s-80s, 1983.

Polla, L. L., et al., "Melanosomes Are a Primary Target of Q-Switched Ruby Laser Irradiation in Guinea Pig Skin," *The Journal of Investigative Dermatology*, 89:281-286, 1987.

Riggle, Grant C., "Laser Effects on Normal and Tumor Tissue," *Laser Applications in Medicine and Biology*, 1:35-63, 1971.

Shimbashi, T. and Kojima, T., "Ruby Laser Treatment of Pigmented Skin Lesions," *Aesthetic Plastic Surgery*, 19: 225-229, 1995.

Stratton, K., et al., "Biological Effects of Laser Radiation II: ESR Studies of Melanin Containing Tissues after Laser Irradiation," *Northeast Electronics Research and Engineering Meeting—NEREM Record—1965*, IEEE Catalogue No. F-60, (Nov. 4, 1965) pp. 150-151.

Taylor, C. R., et al., "Treatment of Tattoos by Q-Switched Ruby Laser," *Arch Dermatol*, 126:893-899, 1990.

Tuchin, Valery V., "Laser Light Scattering in Biomedical Diagnostics and Therapy," reprinted from *Journal of Laser Applications*, vol. 5(2,3), pp. 43-60 (Fall 1993) Laser Institute of America, Toledo, Ohio.

Watanabe, S., et al., "Comparative Studies of Femtosecond to Microsecond Laser Pulses on Selective Pigmented Cell Injury in Skin," *Photochemistry and Photobiology*, 53:757-762, 1991.

Watanabe, S., et al., The Effect of Pulse Duration on Selective Pigmented Cell Injury by Dye Lasers, *The Journal of Investigative Dermatology*, 88:523, 1987.

Welch, A. J., et al., "Evaluation of Cooling Techniques for the Protection of the Epidermis during ND-YAG Laser Irradiation of the Skin," *Neodymium-YAG Laser in Medicine and Surgery*. New York, Elsevier, 1983, pp 196-204.

Yules, R. B., et al., "The Effect of Q-Switched Ruby Laser Radiation on Dermal Tattoo Pigment in Man," *Arch Surg*, 95:179-180, 1967.

Zeitler, E. and Wolbarsht, M. L., "Laser Characteristics that Might be Useful in Biology," *Laser Applications in Medicine and Biology*, 1:1-16, 1971.

* cited by examiner

METHOD AND APPARATUS FOR EMR TREATMENT

PRIOR APPLICATION

This Application claims priority from provisional application Ser. No. 60/258,855 filed Dec. 28, 2000.

FIELD OF THE INVENTION

This invention relates to methods and apparatus for using electromagnetic radiation (EMR) for various therapeutic treatments and more particularly to methods and apparatus for dermatological treatment by use of spatially confined and concentrated EMR to create areas of treatment or damage substantially surrounded by areas of sparing.

BACKGROUND OF THE INVENTION

Various forms of electromagnetic radiation, particularly optical radiation, both coherent and non-coherent, have been utilized for many years for a variety of medical treatments, and in particular for dermatology treatments. Such treatments include, but are by no means limited to, removal of unwanted hair, skin rejuvenation, removal of vascular lesions, acne treatment, treatment of cellulite, pigmented lesions and psoriasis, tattoo removal, treatment of skin and other cancers, etc. Most of these treatments have involved in one way or another the use of a process known as selective photothermolysis (See for example Anderson R R, Parrish J., Selective photothermolysis: Precise microsurgery by selective absorption of the pulsed radiation. Science 1983; 220: 524–526), this process involving irradiating a target area to be treated with radiation at a wavelength preferentially absorbed by a chromophore, either a natural chromophore or artificially introduced chromophore, in the target area, the heating of the chromophore either directly or indirectly effecting the desired treatment.

While these techniques are useful for many of the indicated applications, these techniques have a number of significant limitations. First, treatments which are performed over a relatively large area, such as skin rejuvenation and hair removal, particularly skin rejuvenation, can cause varying degrees of skin damage over a substantial treatment area. In particular, such treatments can sometimes result in a detachment of skin layers. These relatively large areas of skin damage can frequently take several weeks or more to heal, and follow-up treatments can normally not be performed during this period. It would be preferable if these procedures could be performed in a manner which would result in smaller, spaced areas of damage which heal more quickly, this enhancing both patient comfort and the ability to more quickly perform follow-up treatments. Further, many treatments, such as for example hair removal and wrinkle removal, only require that the treatment be performed in small portions or regions of a much larger treatment area; however, current techniques of treatment generally require that the treatment be performed over the entire treatment area rather than in only the selected regions of the treatment area requiring treatment.

Another potential problem is the need for a chromophore in the target area which selectively absorbs the applied radiation to generate the heat required for treatment. First, to the extent the regions above the treatment area contain a chromophore which preferentially absorbs or otherwise absorbs the applied radiation, such chromophores are also heated, and care must be exercised in any treatment to assure that such heating does not result in epidermal or dermal damage. Various forms of cooling of such overlying regions, sometimes aggressive cooling, are frequently required to permit such treatments to be performed without damage to the overlying skin. For example, for hair removal or other treatments where melanin is targeted, heating of melanin in the epidermis, particularly at the dermis-epidermis (DE) junction, is a problem. Where the chromophore being targeted is water, substantially all tissue in the treatment area and thereabove will be absorbing the radiation and will be heated, making controlled treatment of a selected body component difficult, and increasing the likelihood of unwanted peripheral damaged.

Another problem with selective photothermolysis is that the wavelength selected for the radiation is generally dictated by the absorption characteristics of the chromophore utilized. However, such wavelengths may not be optimal for other purposes. For example, skin is a scattering medium, but such scattering is far more pronounced at some wavelengths than at others. Unfortunately, wavelengths preferentially absorbed by for example melanin, a frequently used chromophore, are also wavelengths at which substantial scattering occurs. This is also true for the wavelengths typically utilized for treating vascular lesions. Photon absorption in skin also varies over the optical wavelength band, wavelengths dictated by selective photothermolysis frequently being wavelengths at which skin is highly absorbent. The fact that wavelengths typically utilized for selective photothermolysis are highly scattered and/or highly absorbed limits the ability to selectively target body components, and in particular, limits the depths at which treatments can be effectively and efficiently performed. Further, the fact that much of the energy applied to a target region is either scattered and does not reach the body component undergoing treatment, or is absorbed in overlying or surrounding tissue to cause undesired and potentially dangerous heating of such tissue, results in optical dermatology treatments being relatively inefficient. This low efficiency for such treatments means that larger and more powerful EMR sources are required in order to achieve a desired therapeutic result and that additional cost and energy must be utilized to mitigate the effects of this undesired heating by surface cooling or other suitable techniques. Heat management for the more powerful EMR source is also a problem, generally requiring expensive and bulky water circulation or other heat management mechanisms. Further, since chromophore concentration in a target (for example melanin in the hair) varies significantly from target to target and from patient to patient, it is difficult to determine optimum, or even proper parameters for effective treatment of a given target using selective photothermolysis. High absorption by certain types of skin, for example dark skinned individuals or people with very tanned skin, often makes certain treatments difficult, or even impossible, to safely perform. A technique which permitted all types and pigmentations of skin to be safely treated, preferably with little or no pain, and preferably using substantially the same parameters, is therefore desirable.

Still another problem with existing treatment is that the amount of energy which can be applied to the treatment area, even where damage to the epidermis, skin scarring or other damage is not an issue, is frequently limited by pain experienced by the patient. Ideally, EMR dermatology procedures, which are typically for cosmetic purposes, should be painless or substantially painless. While if the procedure is being performed by a physician, pain may be controlled by the use of a local anesthetic, or even by putting the patient to sleep, there are risks in the use of any anesthetic, and the use of needles to administer a local anesthetic is undesirable for cosmetic procedures. It would therefore be preferable if patient pain could be substantially reduced or eliminated without the need for such procedures, while still permitting sufficient radiation to be applied to achieve a desired therapeutic result.

There are also occasions where microsurgery is required or desired on a patient's skin, particularly near the skin surface, where the area to be treated is of a size in the micron range, for example 10 microns, a size which cannot be treated with a scalpel. Existing EMR devices for performing microsurgery are also not adapted for performing surgery on such small targets. A need therefore exists for improved techniques for performing such fine microsurgery.

Further, while EMR techniques are available for treating some of the conditions indicated above, such techniques do not currently exist for treating scars, including acne scars, chicken pox scars and the like, for bumps in the skin resulting from scar tissue, for stretch marks, for treating certain parasites, etc. An effective technique for treating such conditions is therefore needed.

Still another problem is in the removal of tattoos or pigmented lesions, particularly close to the skin surface, where existing techniques frequently result in blistering and other skin problems. An improved technique which would permit the fading of such tattoos or pigmented lesions and/or the ultimate removal thereof in a gentle enough manner so as to not cause damage to the patient's skin or significant patient discomfort is also desirable. Similar techniques for treating various skin blemishes are also desirable.

Finally, while techniques currently exist which are relatively effective in treating large vascular lesions, such techniques are not as efficient in treating spider veins and other small veins. Similar inefficiencies exist where radiation is applied over a relatively large area of a patient's skin where treatment is required in only relatively small portions of such area.

A need therefore exists for an improved method and apparatus for EMR therapeutic treatments, and in particular for optical dermatology treatments, which permit more selective treatment in target areas, and which do not rely on selective photothermolysis so that the wavelengths utilized may be selected so as to be more efficient for delivery of radiation to a desired target volume at a selected depth, and in particular to selected portions of such a target volume, which portions are preferably surrounded by portions which are not treated, and so that proper parameters for treating a given target may be more easily determined.

SUMMARY OF THE INVENTION

In accordance with the above, this invention provides a method and apparatus for performing a treatment on a volume located at area and depth coordinants of a patient's skin, the method involving providing a radiation source and applying radiation from the source to an optical system which concentrates the radiation to at least one depth within the depth coordinants of the volume and to selected areas within the area coordinants of the volume, the at least one depth and the selected areas defining three-dimensional treatment portions in the volume within untreated portions of the volume. The apparatus has the radiation source and an optical system to which radiation from the source is applied, the optical system concentrating the radiation to at least one depth in the volume and to selected areas of the volume, the at least one depth and the areas defining the three-dimensional treatment portions in the volume within untreated portions of the volume. For both the method and apparatus, the ratio of the treatment portions to the volume may be between 0.1% and 90%, but is preferably between 10% and 50%, and more preferably between 10% and 30%. In each instance, the treatment portions may be cylinders, spheres, ellipsoids, solid rectangles or planes of at least one selected size and thickness. The treatment portions may also be spaced lines of a selected length and thickness. The optical system may either apply radiation to all the treatment portions substantially simultaneously or the optical system may apply radiation to at least selected treatment portions sequentially.

The patient's skin over at least one treatment portion may also be pre-cooled to a selected temperature for a selected duration, the selected temperature and duration for pre-cooling preferably being sufficient to cool the skin to at least a selected temperature below normal body temperature to at least the at least one depth for the treatment portions. For selected embodiments, the skin is cooled to at least the selected temperature to a depth below the at least one depth for the treatment portions so that the at least one treatment portion is substantially surrounded by cooled skin. The cooling may continue during the applying of radiation, and for this embodiment, the duration of the applying of radiation may be greater than the thermal relaxation time of the treatment portions. The wavelength for the radiation source is preferably selected so as not to be either highly absorbed or scattered in the patient's skin above the volume on which treatment is to be performed. For deeper depth coordinants, the optical system focuses to a selected depth below the at least one depth of the treatment portions in order to achieve concentration at the desired depth coordinant in the patient's skin. A selected condition in the volume on which treatment is being performed and/or the patient's skin above this volume may be detected, the results of the detecting being utilized during the applying of radiation to control the treatment portions to which radiation is concentrated.

The applied radiation preferably has an output wavelength which is at least in part a function of the at least one depth of the treatment portions. More specifically, the wavelength of the applied radiation may be selected as a function of the applied radiation as follows: depth=0.05 to 0.2 mm, wavelength=400–1880 nm & 2050–2350 nm, with 800–1850 nm & 2100–2300 nm preferred; depth=0.2 to 0.3 mm, wavelength=500–1880 nm & 2050–2350 nm, with 800–1850 nm & 2150–2300 nm preferred; depth=0.3 to 0.5 mm, wavelength=600–1380 nm & 1520–1850 nm & 2150–2260 nm, with 900–1300 nm & 1550–1820 nm & 2150–2250 nm preferred; depth=0.5 to 1.0 mm, wavelength=600–1370 nm & 1600–1820 nm, with 900–1250 mn & 1650–1750 nm preferred; depth=1.0 to 2.0 mm, wavelength=670–1350 nm & 1650–1780 nm, with 900–1230 nm preferred; depth=2.0 to 5.0 mm, wavelength=800–1300 nm, with 1050–1220 nm preferred.

The method and apparatus may also be utilized to treat a variety of medical conditions. Where a vascular lesion at a selected depth is being treated, treatment parameters, including the optical system and the wavelength of the applied radiation are selected so that the at least one depth of the treatment portions are at the depth of the vessel being treated. Similarly, where the treatment is skin remodulation by treatment of collagen or hair removal, treatment parameters, including the optical system and the radiation wavelength are selected so that the at least one depth is the depth of interdermal collagen and the depth of at least one of the bulge and matrix of the hair follicle, respectively. The teachings of this invention may also be used to treat acne, to target and destroy pockets of fat, to treat cellulite, for tattoo removal, for treating pigmented lesions, for treating hypotropic and other scars and other skin blemishes, and for treating various other conditions in the skin.

The optical system utilized in practicing this invention may include an array of optical elements to at least a plurality of which radiation from the source is simultaneously applied, each of the optical elements concentrating the radiation to a selected portion of the volume. Each of the optical elements may for example focus or concentrate to a line of selected length and thickness, the lines for some of the elements being at a selected angle to the lines of other of the elements. The optical system may alternatively include apparatus for scanning radiation applied to optical concentrating components so as to successively focus radiation to N of the treatment portions at a time, where $N \geq 1$. The optical system may instead include adjustable depth optical focusing components, and a positioning mechanism for such optical focusing components which moves the components to focus at successive treatment portions. The apparatus may also include a mechanism which cools the part of the patient's skin at least over the selected area coordinants to a selected temperature, and controls which selectively operate the cooling mechanism to pre-cool this part of the patient's skin for a selected duration before application of radiation and/or during application of radiation. The cooling mechanism and the controls may pre-cool the skin to a temperature and for a duration sufficient to cool the part of the skin to at least a selected temperature below normal body temperature to the at least one depth of the treatment portions or may cool to a depth below the at least one depth of the treatment portions, the treatment portions in the latter case being substantially surrounded by cooled skin. The apparatus may also include a detector for at least one selected condition in the volume and/or in a part of the patient's skin above the volume and the optical system may operate in response to the detector to control the treatment portion of the volume to which radiation is concentrated.

The invention also includes a method and apparatus for performing a treatment on a volume located at an area and depth coordinant of a patient's skin which includes providing a radiation source and pre-cooling the patient's skin over at least part of the area coordinant of the volume to a selected temperature for a selected duration, the selected temperature and duration being sufficient to cool the skin to a depth below the depth coordinant of the volume; and applying radiation to an optical system which concentrates the radiation to at least one depth coordinant and to selected areas within the area coordinants to define treatment portions in the volume, the treatment portions being less than the total volume and each treatment portion being within untreated portions and being substantially surrounded by cooled skin. More specifically, a mechanism may be provided which cools the patient's skin over the area coordinant to the selected temperature and controls may be provided for selectively operating the cooling mechanism to pre-cool the skin for a selected duration before application of radiation and/or during application of radiation, the mechanism and controls cooling to a temperature and for a duration sufficient to cool the skin to at least a selected temperature below normal body temperature to at least a depth below the depth coordinant of the volume. The cooling of the patient's skin by the cooling mechanism may continue during the step of applying radiation and the duration of radiation application may be greater than the thermal relaxation time of each treatment portion.

Finally, the invention includes a method and apparatus for performing a therapeutic treatment on a patient's skin by concentrating applied radiation of at least one selected wavelength at a plurality of selected three-dimensionally located treatment portions, which treatment portions are within non-treatment portions.

The foregoing and other objects, features and advantages of the invention will be apparent from the following more particular description of various embodiments of the invention as illustrated in the accompanying drawings, the same or related reference numerals being used for common elements in the various figures.

IN THE DRAWINGS

DETAILED DESCRIPTION

Figure 22A:
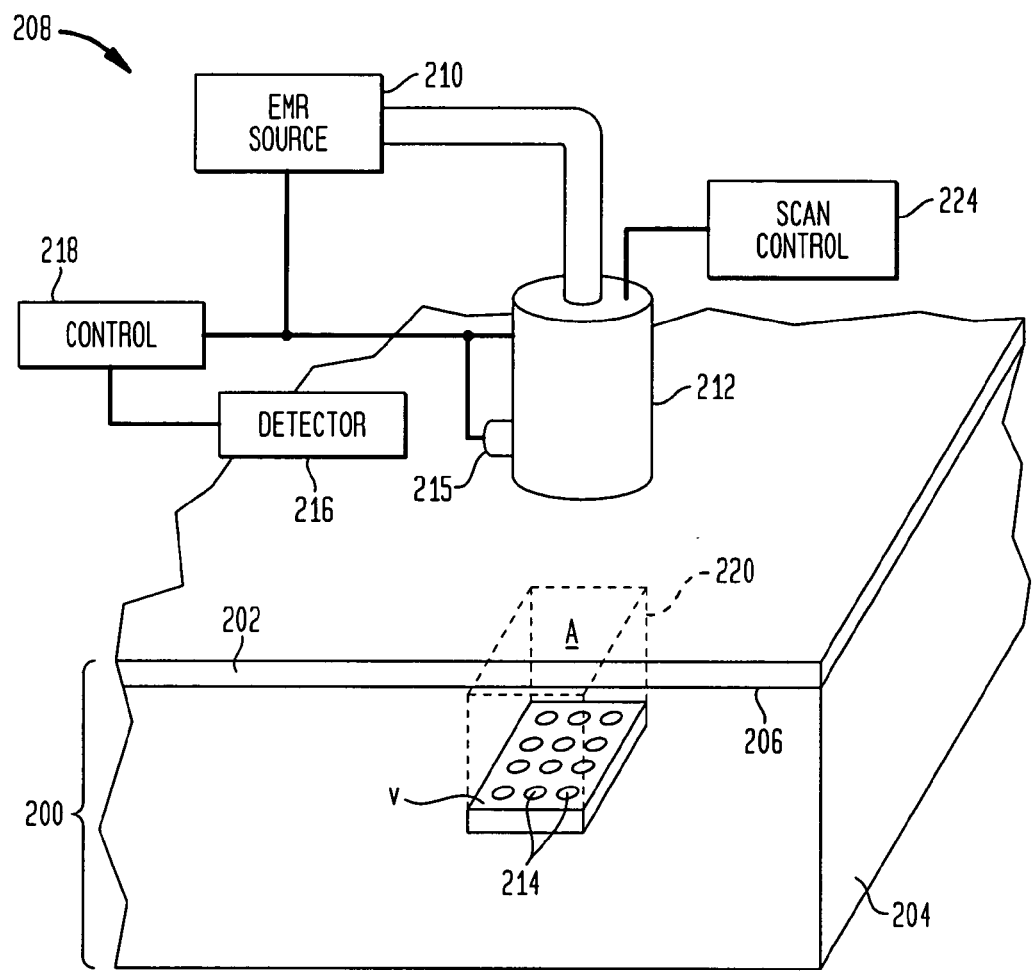
FIGS. 22A and 22B are semi-schematic perspective and side views respectively of a section of a patient's skin and of equipment positioned thereon for practicing the teachings of this invention.
Figure 22B:
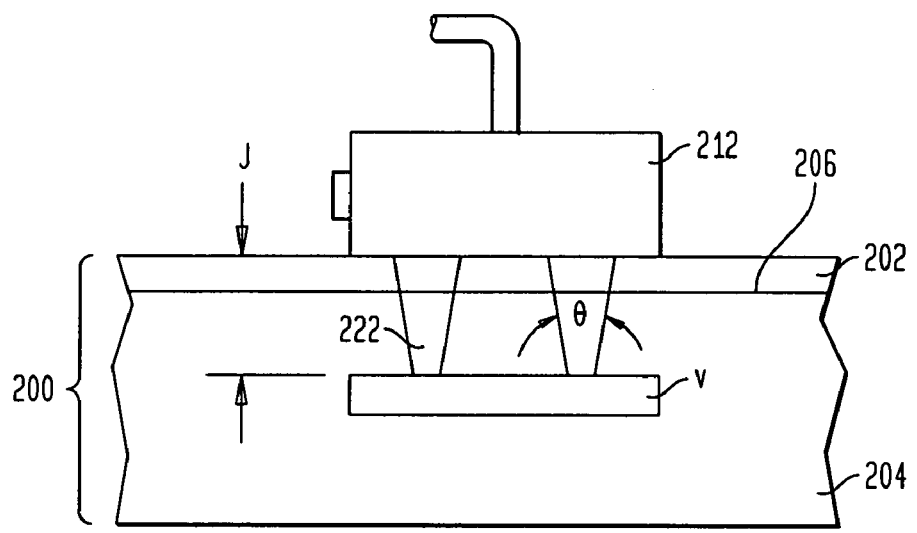

Referring first to FIGS. 22A and 22B, a portion of a patient's skin 200 is shown, which portion includes an epidermis 202 overlying a dermis 204, the junction of the epidermis and dermis being referred to as the dermis-epidermis (DE) junction 206. Also shown is a treatment volume V located at a depth d in the patient's skin and having an area A. Treatment volume V may contain one or more vascular lesions which are to be destroyed or removed, may contain a plurality of hair follicles which are to be either permanently destroyed, or at least be damaged so as to result in temporary hair loss, or which are to be stimulated to cause hair growth, may contain in the area below the DE junction collagen which is to be restructured by various means, for example by being temporarily destroyed to stimulate regrowth, particularly for skin rejuvenation and wrinkle removal, may contain a melanoma to be removed, a vascular lesion, pigmented lesion, port wine stain, psoriasis, scar, or other skin blemish or a tattoo to be removed, or some other bodily component on which optical dermatology procedures are performed.

Also shown is a system 208 for delivering optical radiation to volume V. System 208 includes an EMR source 210, which source may be a coherent light source, such as a solid-state laser, dye laser, diode laser, fiber laser or other coherent light source, or may be an incoherent light source, for example a flash lamp, halogen lamp, light bulb or other incoherent light source used to deliver optical radiation in dermatology procedures. Acoustic, RF or other EMF sources may also be employed in suitable applications. The output from source 210 is applied to an optical system 212, which is preferably in the form of a deliver head in contact with the surface of the patient's skin as shown in FIG. 22B. Where an acoustic, RF or other non-optical EMR source is used as source 210, system 212 would be a suitable system for concentrating or focusing such EMR, for example a phased array, and the term "optical system" should be interpreted, where appropriate, to include such system.

Various embodiments of an optical system 212 are discussed hereinafter and shown in the various figures. Generally, system 212 functions to receive radiation from source 210 and to focus/concentrate such radiation to a focused one or more beams 222 directed to a selected one or more treatment or target portions 214 of volume V, the focus being both to the depth d and spatially in the area A. The energy of the applied EMR is thus concentrated to deliver more energy to target portions 214. Depending on system parameters, portions 214 may be cylinders of selected diameter and thickness, spheres or ellipsoids, and for one embodiment may have a square or rectangular cross-section. The portions of each shape may extend through volume V or may be formed in a single layer or staggered layers thereof. Target portions 214 may also be (a) relatively narrow strips which may either extend through volume V, be formed in a single thin layer in volume V or be in staggered layers of the volume; or (b) may be one or more thin layers formed in volume V. As will be discussed in greater detail hereinafter, optical system 212 may focus to all or a selected subset of portions 214 simultaneously, may contain some type of optical or mechanical-optical scanner for moving radiation focused to depth d to successive portions 214, or may generate an output focused to depth d and be physically moved on the skin surface over volume V, either manually or by a suitable two-dimensional or three-dimensional (including depth) positioning mechanism, to direct radiation to desired successive portions 214. For the two later embodiments, the movement may be directly from portion to portion to be focused on or the movement may be in a standard pattern, for example a grid pattern, with the EMR source being fired only when over a desired portion 214.

A cooling element 215 is also included to cool the surface of skin 200 over treatment volume V. As shown in FIG. 22A and 22B, cooling element 215 acts on optical system 212 to cool the portion of this system in contact with the patient's skin, and thus the portion of the patient's skin in contact with such element. Cooling element 215 may for example be a thermoelectric element, or may be a system for passing water, preferably chilled water, a gas, preferably a chilled gas, and possibly even a cryogenic gas, over such portion of the optical system. Other techniques for cooling the surface of the patient's skin known in the art could also be used. Further, where optical system 212 is not in contact with the patient's skin, cryogenic spray cooling, gas flow or other non-contact cooling techniques may be utilized. A cooling gel on the skin surface might also be utilized, either in addition to or instead of, one of the cooling techniques indicated above.

System 208 also includes an optional detector 216, which may for example be a CCD camera or other suitable detector for a selected characteristic of the patient's skin. The output from detector 216 is applied to a control 218, which is typically a suitably programmed microprocessor, but may be special purpose hardware or a hybrid of hardware and software. Control 218 controls both the turning on and turning off of source 210 and may also control the power profile of the radiation. Control 218 is also applied to optical system 212 to for example control focus depth for the optical system and to control the portion or portions 214 to which radiation is being focused/concentrated at any given time, for example by controlling scanning by the optical system and/or the beam radiating therefrom. Finally, controls 218 are applied to cooling element 215 to control both the skin temperature above the volume V and the cooling duration, both for precooling and during an irradiation.

TABLE 1

| Depth of damage, $\mu m$ | Wavelength range, $\mu m$ | | NA range | | Pulse width range, s |
|---|---|---|---|---|---|
| | broad | preferred | broad | preferred | |
| 50–200 | 400–1880 & 2050–2350 | 800–1850 & 2100–2300 | <3 | 0.2–1 | <2 |
| 200–300 | 500–1880 & 2050–2350 | 800–1850 & 2150–2300 | <3 | 0.2–1 | <10 |
| 300–500 | 600–1380 & 1520–1850 & 2150–2260 | 900–1300 & 1550–1820 & 2150–2250 | <2 | 0.2–1 | <60 |
| 500–1000 | 600–1370 & 1600–1820 | 900–1250 & 1650–1750 | <2 | 0.2–0.6 | <120 |
| 1000–2000 | 670–1350 & 1650–1780 | 900–1230 | <1.5 | 0.2–0.6 | <120 |
| 2000–5000 | 800–1300 | 1050–1220 | <1 | 0.2–0.4 | <300 |

TABLE 2

| Depth of damage, $\mu m$ | Diameter of damage, $\mu m$ | Wavelength $\mu m$ | NA | Pulse width, ms | Energy, J | Focusing depth $\mu m$ |
|---|---|---|---|---|---|---|
| 300 | 50–100 | 2.2 | 0.3–0.5 | <10 | >0.00015 | 400–600 |
| 300 | 50–100 | 1.7 | 0.3–0.5 | <10 | >0.0007 | 400–600 |
| 300 | 50–100 | 1.3 | 0.3–0.5 | <10 | >0.003 | 400–600 |

TABLE 2-continued

| Depth of damage, μm | Diameter of damage, μm | Wavelength μm | NA | Pulse width, ms | Energy, J | Focusing depth μm |
|---|---|---|---|---|---|---|
| 300 | 50–100 | 1.54 | 0.3–0.5 | <10 | >0.0003 | 400–600 |
| 300 | 50–100 | 1.208 | 0.4–1 | <10 | >0.016 | 400–600 |
| 300 | 50–200 | 0.92 | 0.4–1 | <10 | >0.15 | 400–600 |
| 1000 | 50–200 | 1.7 | 0.3–0.4 | <100 | >0.01 | 1100–2000 |
| 1000 | 50–200 | 1.54 | 0.4 | <100 | >0.008 | 1100–2000 |
| 1000 | 50–200 | 1.3 | 0.4 | <100 | >0.1 | 1100–2000 |
| 1000 | 50–200 | 1.208 | 0.4 | <100 | >0.4 | 1100–2000 |

TABLE 3

| Depth of damage, μm | Diameter of damage, μm | Wavelength μm | NA | Pulse width, ms | Power, W | Focusing depth μm |
|---|---|---|---|---|---|---|
| 500–1000 | 200–1000 | 2.2 | 0.3–0.5 | >100 | >0.5 | 600–1500 |
| 500–1000 | 200–1000 | 1.7 | 0.3–0.5 | >100 | >1.5 | 600–2000 |
| 500–1000 | 200–1000 | 1.208 | 0.3–0.6 | >3000 | >1.0 | 600–2000 |
| 500–1000 | 400–1200 | 0.92 | 0.3–0.6 | >3000 | >25.0 | 600–2000 |
| 2000–3500 | 1000–2000 | 1.208 | 0.3–0.4 | >10000 | >1.5 | 4000–6000 |

In accordance with the teachings of this invention, system 208 controls a variety of parameters of the applied radiation. Data in Tables 1–3 were found based on Monte-Carlo modeling of photon propagation in the skin using standard parameters of skin scattering and absorption for different wavelength. These parameters include, but are by no means limited to:

1. The shape of treatment portions 214. Each of these portions may be a thin disk as shown, may be an elongated cylinder which may for example extend from a first depth closer to DE junction 206 to a second deeper depth or, as will be discussed later in conjunction with various optical systems to be described, may be a line focus, each of the lines having a selected length, width and orientation and adjacent lines being spaced by a selected amount. The orientation of the lines for the portions 214 in a given application need not all be the same, and some of the lines may, for example, be at right angles to other lines (see for example FIGS. 7A and 7B). Lines can by oriented around a treatment target for greater efficacy. For example the lines can be perpendicular to a vessel or parallel to a wrinkle. Portions 214 may also be spherical, ellipsoidal and at least for one embodiment, may be a solid square or rectangle of selected thickness. The shape of portion 214 is dictated by the combined parameters of the focused optical signal applied thereto, with the duration of application and to a lesser extent the wavelength of the signal being significant factors in determining the shape of the targeted portions. For example, it has been found that with a 1720 nm laser operating at roughly 0.5 J to 2 J and having a pulse duration of 0.5 to 2 ms, a generally cylindrically shaped portion 214 is obtained. Conversely, with a 1250 nm laser operating in the same energy range and having a pulse duration of 0.5 to 3 seconds, with an average of 1 second, generally spherically-shaped target portions are obtained. The parameters for obtaining a particular portion shape may be determined in a variety of ways, including empirically. By suitable control of wavelength, focusing, spot size at the surface and other parameters, the portions 214, regardless of shape, may extend through volume V, may be formed in a single thin layer of volume V or may be staggered so that, for example, adjacent portions 214 are in different thin layers of volume V. The pattern of the target portions in volume V may also vary with application. Further, target portions 214 may also be (a) relatively narrow stripes which may either extend through volume V, be formed in a single thin layer or be staggered in different thin layers, with for example adjacent stripes being in different layers; or (b) may be one or more thin layers formed in volume V. While all of the prior configurations for target portion 214 could be formed either serially or in parallel, the last configuration with multiple thin layers in the volume V would probably need to be formed serially. The geometry of portions 214 controls the thermal damage in the treatment portion. Since a sphere provides the greatest gradient, and is thus the most spatially confined, it provides the most localized biological damage, and may therefore be the preferred target shape for applications where this is desirable.

2. The size of the treatment portions 214. For a depth of approximately 1 mm into the patient's skin, the minimum diameter of a portion 214, or the minimum width of a line 214, is estimated to be approximately 100 microns; however, much larger portions, several mm's or more, are possible. For greater depths, the minimum sizes will be greater.

3. Center to center spacing between portions 214. The center to center spacing is determined by a number of factors, including the size of portions 214 and the treatment being performed. Generally, it is desired that the spacing between adjacent portions 214 be sufficient to protect the patient's skin and facilitate healing of damage thereto, while still permitting the desired therapeutic effect to be achieved. In one application, as little as 4% of the volume V was damaged (i.e. a 4% fill factor); however, the damaged portions 214 would typically cover substantially more of treatment volume V. While theoretically, the ratio of the combined volume of treatment portions 214 to the volume V (also sometimes referred to as the fill factor) could be 0.1% to 90%, a preferred range for fill factor is 10% to 50% for some applications and 10% to 30% for most applications. It is important that there be at least some area of sparing around each of the islands or areas of treatment/damage 214 and that this area of sparing be sufficient to permit the skin to recover, such recovery being facilitated by melanosome migration.

4. The depth d for the volume V. While it may be difficult to achieve a small focal spot 214 at a depth much below 1 mm in a scattering medium such as skin, focussing at depths of up to 4 mm, and perhaps even more, may be possible so long as a tight focus is not required and a larger portion size 214, perhaps several millimeters, is acceptable.

5. Focus Depth. While as may be seen from Table 1, depth d for volume V and the focal depth of optical system 212 are substantially the same when focussing to shallow depths, it is generally necessary in a scattering medium such as skin to focus to a greater depth, sometimes a substantially greater depth, in order to achieve a focus at a deeper depth d. The reason for this is that scattering prevents a tight focus from being achieved and results in the minimum spot size, and thus maximum energy concentration, for the focused beam being at a depth substantially above that at which the beam is focussed. The focus depth can be selected to achieve a minimum spot size at the desired depth d based on the known characteristics of the skin.

6. Wavelength. Both scattering and absorption are wavelength dependent. Therefore, while for shallow depths a fairly wide band of wavelengths can be utilized while still achieving a focused beam, the deeper the focus depth, the more scattering and absorption become factors, and the narrower the band of wavelengths available at which a reasonable focus can be achieved. Table 1 indicates preferred wavelength bands for various depths, although acceptable, but less than optimal, results may be possible outside these bands.

7. Pulse Width. Normally the pulse width of the applied radiation should be less than the thermal relaxation time (TRT) of each of the targeted portions 214, since a longer duration will result in heat migrating beyond the boundaries of these portions. Since the portions 214 will generally be relatively small, pulse durations will also be relatively short as indicated in Table 1. However, as depth increases, and the spot sizes thus also increase, maximum pulse width or duration also increase. Again, the values given in Table 1 are maximum values for a given spot size and shorter pulses may be used. Generally, thermal diffusion theory indicates that pulse width $\tau$ for a spherical island should be $\tau < 500 \, D^2/24$ and the pulse width for a cylindrical island with a diameter D is $\tau < 50 \, D^2/16$. Further, the pulsewidths can sometimes be longer than the thermal relaxation time of the target portion 214 if density of the targets is not too high, so that the combined heat from the target areas at any point outside these area is well below the damage threshold for tissue at such point. Also, as will be discussed later, with a suitable cooling regimen, the above limitation may not apply, and pulse durations in excess of the thermal relaxation time for a damage portion 214, sometimes substantially in excess of TRT, may be utilized.

8. Power. The required power from the radiation source depends on the desired therapeutic effect, increasing with increasing depth and cooling and with decreasing absorption due to wavelength. The power also decreases with increasing pulse width.

9. Cooling. Typically cooler 215 is activated before source 210 to precool the patient's skin to a selected temperature below normal skin temperature, for example 0 to 10° C., to a depth of at least DE junction 206, and preferably to depth d to protect the entire skin region 220 above volume V. However, in accordance with the teachings of this invention, if precooling extends for a period sufficient for the patient's skin to be cooled to a depth below the volume V, and in particular if cooling continues after the application of radiation begins, then heating will occur only in the radiated portions 214, each of which portions will be surrounded by cooled skin. Therefore, even if the duration of the applied radiation exceeds TRT for portions 214, heat from these portions will be contained and thermal damage will not occur beyond these portions. Further, while nerves may be stimulated in portions 214, the cooling of these nerves outside of portions 214 will, in addition to permitting tight control of damage volume, also block pain signals from being transmitted to the brain, thus permitting treatments to be effected with greater patient comfort, and in particular permitting radiation doses to be applied to effect a desired treatment which might not otherwise be possible because of the resulting pain experienced by the patient. This cooling regimen is an important feature of the applicants invention.

10. Numerical Aperture. Numerical aperture is a function of the angle $\theta$ for the focused radiation beam 222 from optical device 212. It is preferable that this number, and thus the angle $\theta$, be as large as possible so that the energy at portions 214 in volume V where radiation is concentrated is substantially greater than that at other points in volume V (and in region 220), thereby minimizing damage to tissue in region 220, and in portions of volume V other than portions 214, while still achieving the desired therapeutic effect in the portions 214 of volume V. Higher numerical aperture of the beam increases safety of epidermis, but it is limited by scattering and absorption of higher angel optical rays. As can be seen from Table 1, the possible numerical aperture decreases as the focus depth increases.

Thus, by judicious selection of the various parameters indicated above and others, one or more focused radiation beams 222 may be achieved to create islands of treatment/damage 214 in a treatment volume V at a selected depth d in the patient's skin. Preferred ranges of parameters for achieving these objectives at various depths are provided in Table 1. Table 2 and Table 3 illustrate ranges of parameters at various depths for short pulses (i.e., pulses of less than 10 ms for superficial small targets and less than 100 ms for deeper depths) and for long pulses respectively. The values in Table 2 assume that deep cooling through volume V as described above is not being provided so that the pulse duration is limited by the thermal relaxation time of damage portions 214. Thus, at shorter depths, where smaller spot or focus areas can be achieved, for example a spot having a diameter of 50 $\mu$m, as assumed in Table 2, pulse widths of less than 10 ms are required and other parameters are selected accordingly. Conversely, for deeper depths, tight focus cannot be achieved because of scattering, resulting in a significantly larger diameter for damage portions 214, and thus a larger thermal relaxation time for these portions. Therefore, substantially longer pulse widths can be provided, permitting required energy to achieve the therapeutic effect to be provided over a longer time interval. This facilitates removal of heat from region 220, and in particular from the epidermal portion 202 thereof and from DE junction 206. It also permits a lower peak power source 210 to be utilized. From Table 2, 3 it is also noted that the focus depth is indicated as greater than the depth d of the damage portions 214. The reasons for this have been discussed above.

While controls 218 can be preprogrammed to focus on selected portions 214 in target volume V, another option is to use feedback, either mechanically obtained by use of detector 216, or obtained by an operator, generally optically, but possibly using other of the operator senses such as touch or hearing, to control the portions 214 in volume V which are focused on. Assuming, for example, that detector 216 is a CCD imaging device, the location of hair follicles, vascular lesions, or other targeted components in volume V can be located and focused beams 222 specifically directed to the locations of such components. Thus, assuming a hair removal treatment, detector 216 could locate each hair follicle at the surface above volume V, and then focus a beam 222 to each such follicle at a selected depth, for example, a depth of 1 mm where stem cells are located. The beam could also be focused to an extended depth along the follicle, for example, 0.7–3 mm to assure destruction of all elements within the follicle required for permanent or substantially permanent hair removal, for example, destruction of follicle stem cells, without substantially damaging dermal tissue surrounding the follicle or damage to the follicle matrix. This result is most easily achieved if the cooling technique discussed above is utilized, with cooling extending below the treatment volume V so that each follicle being treated is surrounded by cooled dermal tissue.

Feedback could also be used to track a blood vessel or other vascular structure being treated or to track a wrinkle or wrinkles to be treated by collagen restructuring. Further, while focused beams 222 can be automatically positioned in response to outputs from detector 216 by control 218, such feedback can also be achieved by the operator manually adjusting the position of optical system 212 to track and treat hair follicles, vascular structures, wrinkles or the like.

More specifically, the scanner used could include three low power laser diodes, preferably of different colors, used for detection and one high power laser diode used for treatment. The scanner can, for example, be utilized both to detect the location of the blood vessel and the depth of the blood vessel. One of the three diodes used for detection may be a high power diode which can be operated in either a detection or treatment mode and detection, in some instances, may be performed by only one or two diodes, which diode or diodes may be also used for treatment in some cases. A suitable scanner can be used to move the detectors and/or treatment diode over a selected pattern. However, while galvanic scanners have been used in the past, a contact scanner is required for this application, since the desired focusing of the beam requires contact, something which is not possible with a galvanic scanner. Again, the scanner can be programmed to trace a particular pattern to locate targets, and may be programmed to follow a target once located, for example a vein, or the scan may be manually controlled. Where the scan is following a selected target, for example a blood vessel, irradiation may occur at selected points along the blood vessel. It is generally necessary to coagulate a blood vessel at a selected one or more points along the vessel in order to stop blood flow therein and kill the vessel. It should not be necessary to irradiate the entire vessel in order to effect destruction thereof.

Where a scanner is being used, the area scanned can be projected on a screen, providing effective magnification, which facilitates either the selection of desired target points in a programmed scan or the performance of a scan along a desired target such as a blood vessel. Multiple detectors, which may be filtered to provide different colors, can be utilized for detecting the depth of a target, for example the blood vessel, so that light can be focused to the appropriate depth for treatment. Thus, scanning can be in three dimensions. Since depth is to some extent controlled by wavelength, a fiber laser, the output wavelength of which is programmable over a limited range, may be utilized to control skin depth both for detection and treatment. In each instance, the treatment may be effected solely by focusing radiation to a selected point, water at the point normally being what is heated, or by the effect of such focusing coupled with selective absorption by the desired target at the wavelength utilized. The chromophor, while typically water, could also be blood or melanin. Further, when treating blood vessels, since there is no need for hemoglobin as a chromophore, the vessel can be compressed during treatment, for example by applying pressure to the vessel. This can permit denaturation and shrinkage of the vessel wall, which can result in a more permanent closure of the vessel and in the potential to permanently close larger vessels. The location and size of the islands of treatment/damage can be adjusted for different size, type and location of vessel. Similarly, for hair removal, since melanin need not be targeted, there is no requirement for high melanin content in the hair shaft or follicle, facilitating the easier treatment of gray and blond hair.

For port wine stains, wavelength can be in a range of 0.9 to 1.85 $\mu$m for water absorption or 0.38 to 1.1 $\mu$m for hemoglobin absorption with a fill factor of 10% to 80%, and preferably, 30% to 50%. The light source can be an arc lamp with filtering and masking.

The teachings of this invention are also particularly adapted for skin rejuvenation treatments by collagen regeneration. In such treatments, since collagen is not itself a chromophor, a chromophor such as water in the tissues or blood in the papillary dermis or below typically absorbs radiation and is heated to heat the adjacent collagen, causing selective damage or destruction thereof which results in collagen regeneration. Perturbing blood vessels in the region can also result in the release of fibroblasts which trigger the generation of new collagen. While such treatments may be made only along the line of a wrinkle or other blemish to be treated, such treatment is typically performed over a relatively large area undergoing treatment. In accordance with the teachings of this invention, such treatments can be more effectively performed by heating selective portions 214, with perhaps a 30% to 50% fill factor, resulting in significant collagen regeneration with less trauma and pain to the patient. Such procedure may be performed over a relatively large area A or, utilizing techniques similar to those discussed above for blood vessels, may be performed by periodically firing a beam when over a wrinkle, the beam being traced in a predetermined pattern and fired only when over selected points on the wrinkle, or being moved to track a wrinkle and periodically fired while thereover. Also, as for other treatments where the teachings of this invention are employed, healing occurs relatively quickly so that a subsequent treatment, to the extent required, might generally be performed within a few weeks of an initial treatment, and certainly in less than a month.

Typically, a bump in the skin occurs when collagen is heated, the bump resulting from contraction of the collagen. Thus, this technique can be used not only to remove wrinkles but also to remove other skin blemishes such as acne or chicken pox scars or other scars in the skin and may also be utilized for treating cellulite. While the bump may recede after approximately a month, the heating also increases the thickness-to-length ratio of the collagen in the area, thus increasing the collagen thickness, resulting in much of the improvement from skin rejuvenation/blemish removal being reasonably permanent.

Other skin blemishes treatable by the teachings of this invention include stretch marks, which differ from wrinkles in that these marks are substantially flush with the surface, the collagen shrinkage and regeneration as a result of heating reducing these marks. Hypotropic scarring, the raised scars which occur after surgery or certain wounds, can also be treated by reducing blood flow to the vessels of the scar in much the same way that port wine stains are treated above.

In addition to hair removal, treatment of vascular lesions, and skin resurfacing, the teachings of this invention can also be used to target and destroy a sebaceous gland or glands, for example to treat acne, to target and destroy pockets of subcutaneous fat, to treat cellulite and to do skin resurfacing on areas where such treatments cannot currently be performed, for example neck and hands, where the damage caused using standard skin resurfacing techniques does not normally heal. The treating of only small islands in such areas should leave sufficient undamaged skin structure for healing to occur. The teachings of this invention may, as indicated above, also be utilized for tattoo removal, for treating pigmented lesions, for treating hypotropic and other scars, stretch marks, acne and chicken pox scars and other skin blemishes and for treating various other conditions which may exist in the patient's body at depths of less than approximate 4 mm, for example, various skin cancers and possibly PFB. For skin tumors, a combination may be used of a feedback system that localizes the position of the tumor and a robotic system that insures complete thermal destruction of the tumor. Psoriasis may be treated in substantially the same way with substantially the same parameters as for port wine stain. The teachings may also be used to treat intredermal parasites such as larva migrans, which can be detected and selectively killed using the teachings of the invention.

There are three general ways in which the invention may be utilized for tattoo removal. The first is by using a wavelength or wavelengths absorbed by the tattoo ink, preferably with short, high fluence pulses, to break up or destroy the ink in and between cells. The second technique involves destroying the cells containing the ink, targeting either the ink or water in the cells, causing the ink to be released and removed by the body's lymphatic system. Here long pulses in the millisecond to second range, having low power and high energy, would typically be utilized. In a third technique, an ablation laser would be used to drill 1 to 2 mm spots into the tattoo, ablating or vaporizing both cells and tattoo ink in these areas. With a small fill factor, in for example the 10% to 80% range, and preferable the 10% to 30% range, such small damage spots heal well, permitting the tattoo to be progressively lightened and ultimately removed for each of the three treatments. A randomized pattern on each treatment is also preferable to interference of the removal pattern.

A particular problem for which the teachings of this invention are particularly adapted is the treating of birthmarks or other pigmented lesions in the epidermis. Such lesions are generally difficult to treat without blistering using conventional treatment. By using islands of damage with a fill factor of 1% to 50%, and preferably 10% to 30%, and with a spot size of 100 microns to ½ mm, it is possible to treat such lesions without scarring. Since the treatment in this case is so close to the surface, focusing is not necessary. A similar treatment, with similar fill factor could be used for treating port wine stains or tattoos, but in either of these cases, focusing would be required since the treatment is at a greater depth. In all cases, a first treatment might result in only the lightening of the treated area. Once the treated portion has healed, which generally would occur in a few weeks to a month with an islands of damage treatment, one or more additional treatments can be performed to further lighten the treated area until the lesion, port wine stain, tattoo or the like is removed. In each instance, dead cells resulting from the treatment containing melanosites, ink or the like, would be removed by the body, normally passing through the lymphatic system.

Thus, a technique has been provided (a) which permits various therapeutic treatments on a patient's body at depths up to approximately 4 mm, (b) which permits only islands of damage in three dimensions to occur, thereby facilitating healing (by permitting continued blood flow and cell proliferation between skin layers and islands of damage 214) and reducing patient discomfort, (c) which permits targeting of specific components for treatment without damage to surrounding parts of the patient's body, thereby more efficiently using the applied radiation while also reducing peripheral damage to the patient's body as the result of such treatment (d) which permits treatment of all skin types using substantially the same parameters for a given treatment, thereby simplifying treatment set-up and treatment safety, and (e) which permits the wavelength utilized for treatment to be optimally selected for the depth of treatment, rather than being restricted to a wavelength optimally absorbed by a targeted chromophore. In fact, while the wavelengths selected for the teachings of this invention normally have significant water absorption, one of the criteria in selecting wavelengths is that they are not, particularly for deeper depths, highly absorbed, even by water, so that the radiation can reach desired depths without losing substantial energy/photons to absorption. The concentration of photons/energy at target portions 214 increases energy at these portions more than enough to compensate for reduced absorption at the wavelength utilized. This invention thus provides an entirely new and novel technique for performing such treatments.

Figure 19:
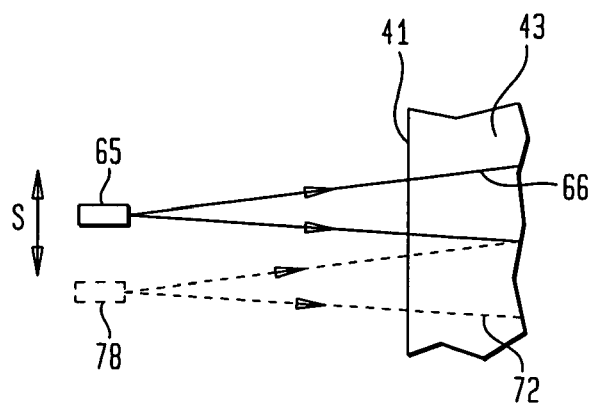
Figure 20:
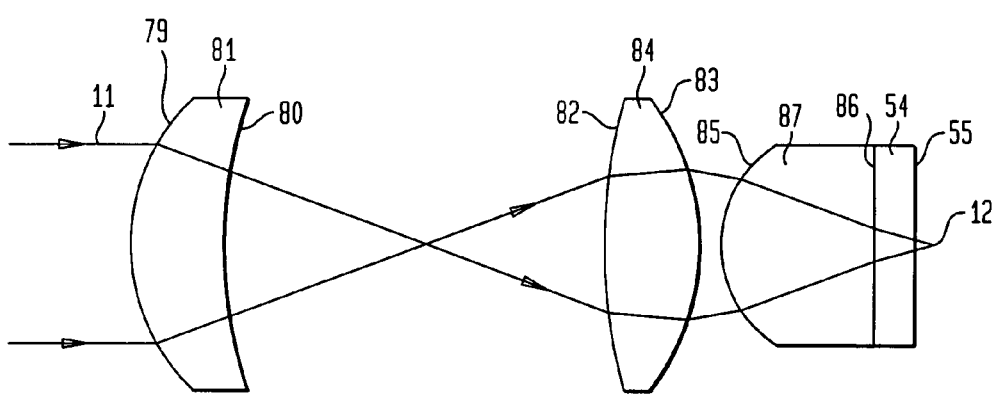
FIGS. 20 and 21 are side views of two different variable focus optical system suitable for use in practicing the teachings of this invention.
Figure 21:
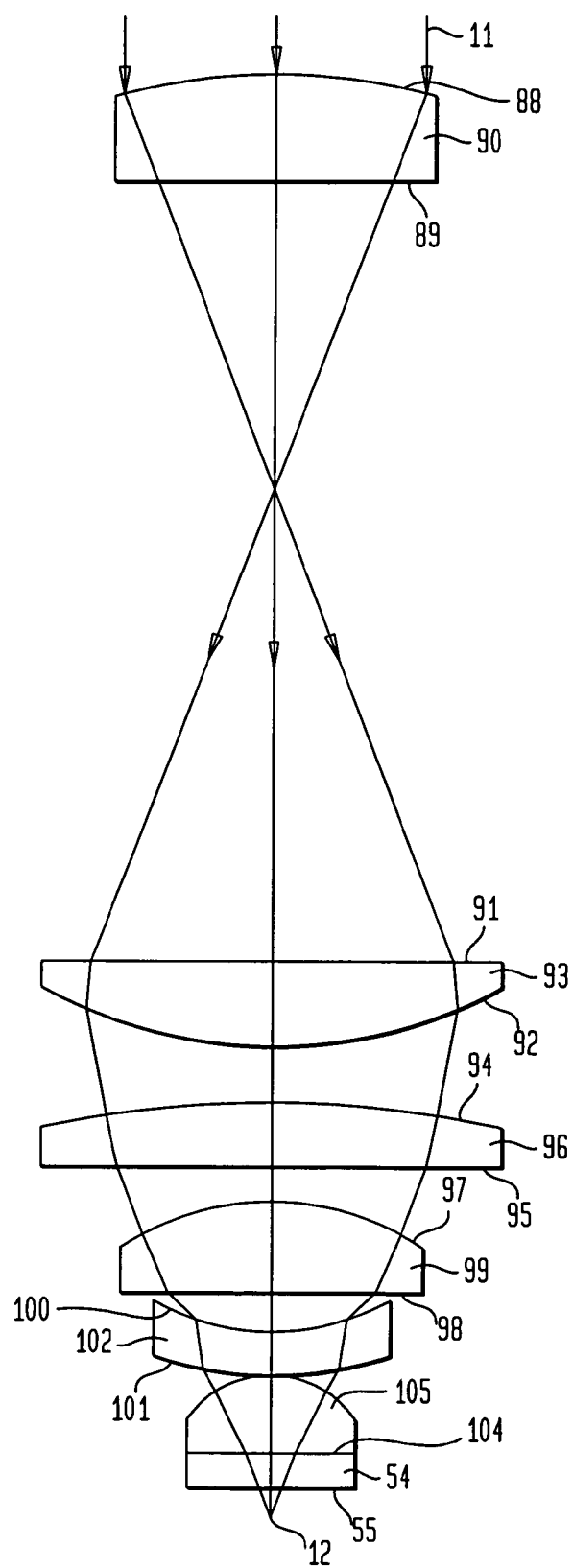

FIGS. 1–21 illustrates various optical components suitable for use in optical system 212. In these figures FIGS. 1–9B illustrate various systems for delivering radiation in parallel to a plurality of target portions 214. The arrays of these figures are typically fixed focus arrays for a particular depth d. This depth may be changed either by using a different array having a different focus depth, by selectively changing the position of the array relative to the surface of the patient's skin or to target volume V or by controlling the wavelength(s) of the radiation. FIGS. 10–13 show various optical objective arrays which may be used in conjunction with the scanning or deflector systems of FIGS. 14–19 to move to successive one or more focused portions 214 within target volume V. Finally, FIGS. 20 and 21 show two different variable focus optical systems which may, for example, be moved mechanically or manually over the patient's skin to illuminate successive portions 214 thereon.

Figure 1:
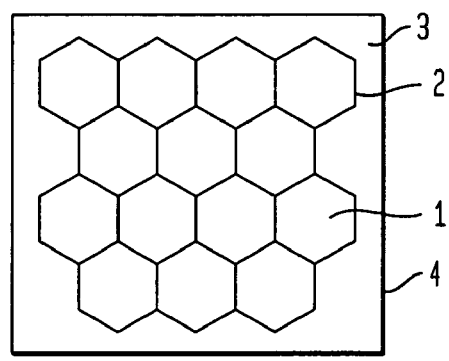
FIGS. 1–1B are top views of three optical systems involving arrays of optical elements suitable for use in delivering radiation in parallel to a plurality of target portions.
Figure 1A:
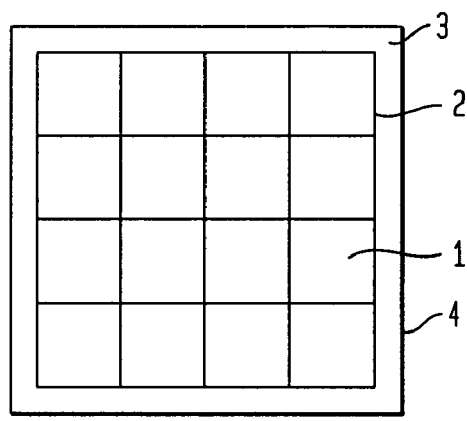
Figure 1B:
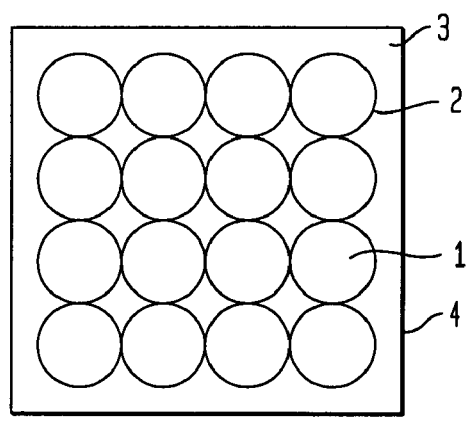

Referring to these figures in greater detail, FIGS. 1, 1A and 1B show a focusing element 1 on a substrate 3, the focusing element having a border which is in a hexagonal pattern (FIG. 1), a square pattern (FIG. 1A), and a circular or elliptical pattern (FIG. 1B).

Standard optical materials can be used for these elements. While the hexagonal and square patterns of FIG. 1 and FIG. 1A can completely fill the working area of the focusing element plate 4, this is not true for the element pattern of FIG. 1B. Radiation from source 210 would typically be applied simultaneously to all of the focusing elements 1; however, the radiation could also be applied sequentially to these elements by use of a suitable scanning mechanism, or could be scanned in one direction, illuminating/irradiating for example four of the elements at a time.

Figure 2:
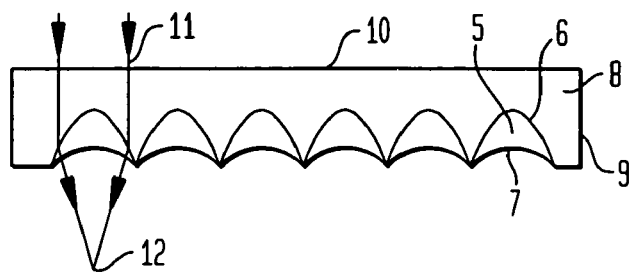
FIGS. 2–3C are side views of various lens arrays suitable for delivering radiation in parallel to a plurality of target portions.
Figure 2A:
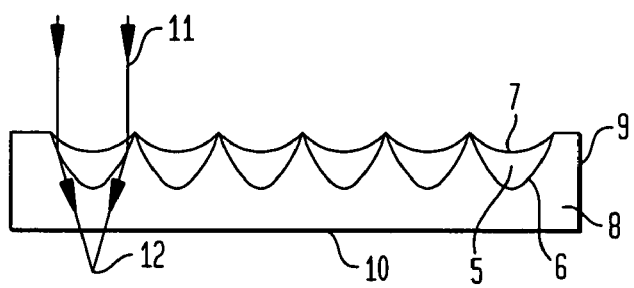

FIGS. 2 and 2A are cross-sectional views of a microlens system fused in a refracting material 8, for example, porous glass. The refractive index for the material of lenses 5 must be greater than the refractive index of refracting material 8. In FIG. 2, beam 11 initially passes through planar surface 10 of refracting material 8 and is then refracted both by primary surface 6 and by secondary surface 7 of each microlens 5, resulting in the beam being focused to a focal point 12. The process is reversed in FIG. 2A, but the result is the same.

Figure 2B:
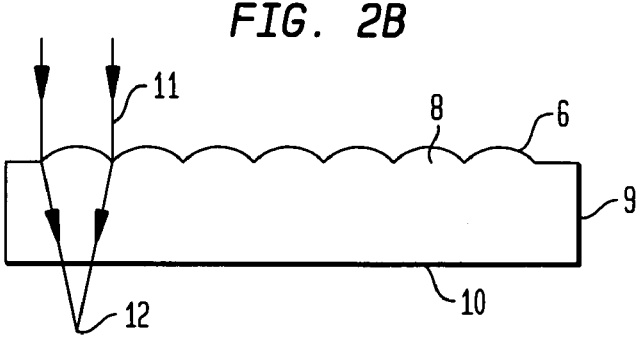
Figure 2C:
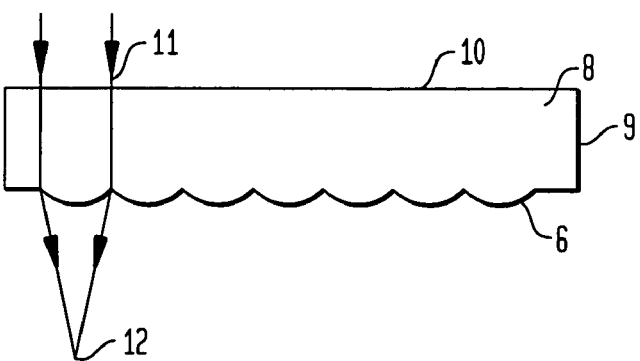

In FIGS. 2B and 2C, the incident beam 11 is refracted by a primary lens surface 6 formed of the refracting material 8. Surfaces 6 and 7 for the various arrays can be either spherical or aspherical.

Figure 3:
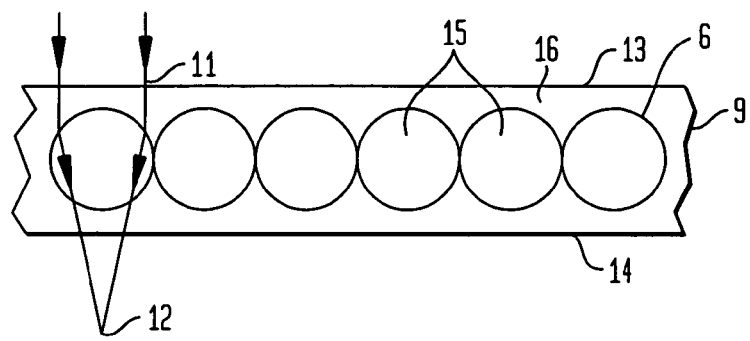
Figure 3A:
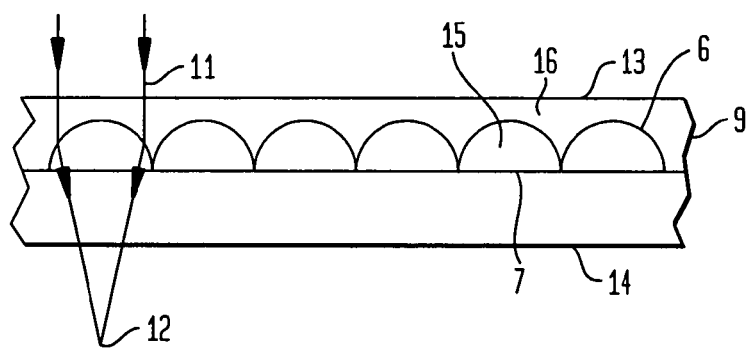
Figure 3B:
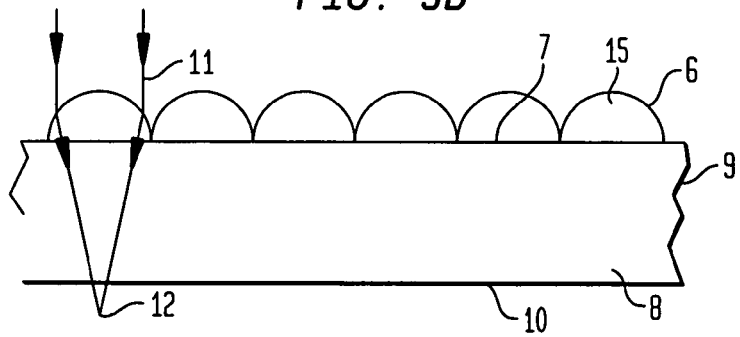
Figure 3C:
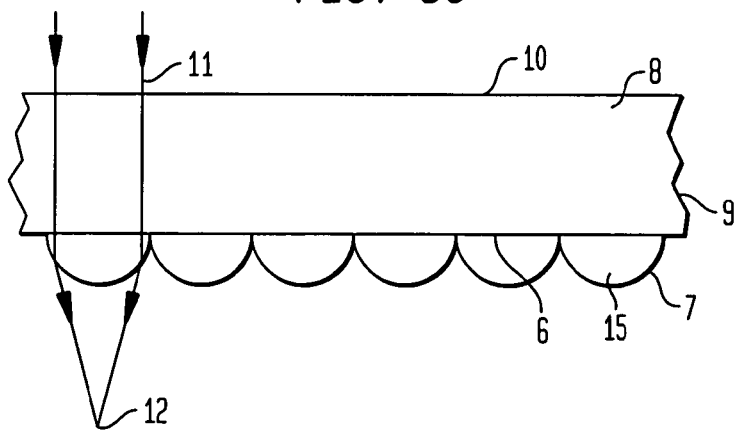

In FIGS. 3 and 3A, the lens pieces 15 are mounted to a substrate and are in an immersion material 16. The refraction index of lens pieces 15 are greater than the refraction index of immersion material 16. Immersion material 16 can be in a gas (air), liquid (water, cryogen spray) or a suitable solid Gas and liquid can be used for cooling of the skin. The immersion material is generally at the primary and secondary plane surfaces, 13 and 14, respectively. In FIG. 3A, the primary surface 6 and secondary surface 7 of each lens piece 15 allows higher quality focusing to be achieved. For FIGS. 3B and 3C, the lens pieces 15 are fixed on a surface of a refracting material 8, the embodiment of FIG. 3C providing a deeper focus than that of FIG. 3B, or that of any of other arrays shown in FIGS. 3A–3C for a given lens 15. The lens arrays shown in FIGS. 3A–3C are a preferred lens arrays for practicing the teachings of this invention.

Figure 4:
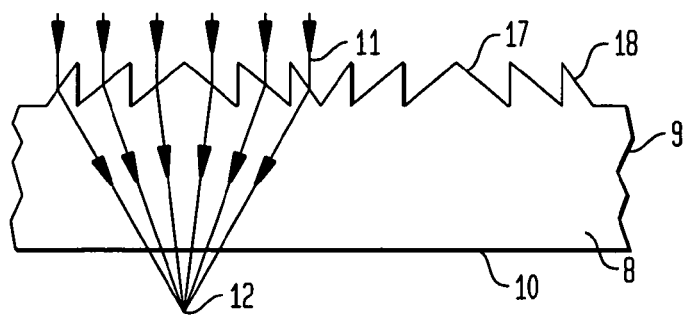
FIGS. 4–4C are side views of Fresnel lens arrays suitable for delivering radiation in parallel to a plurality of target portions.
Figure 4A:
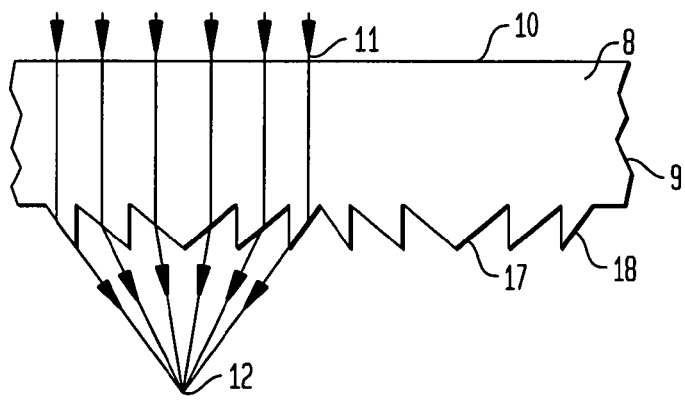
Figure 4B:
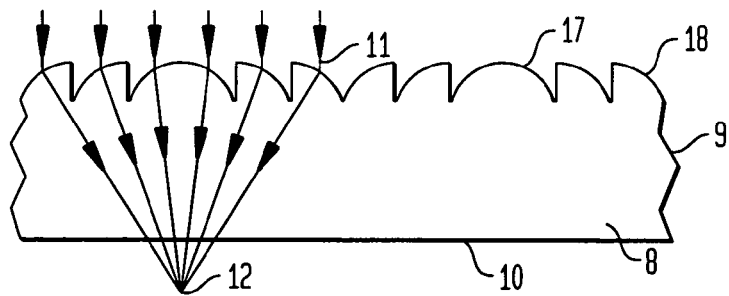
Figure 4C:
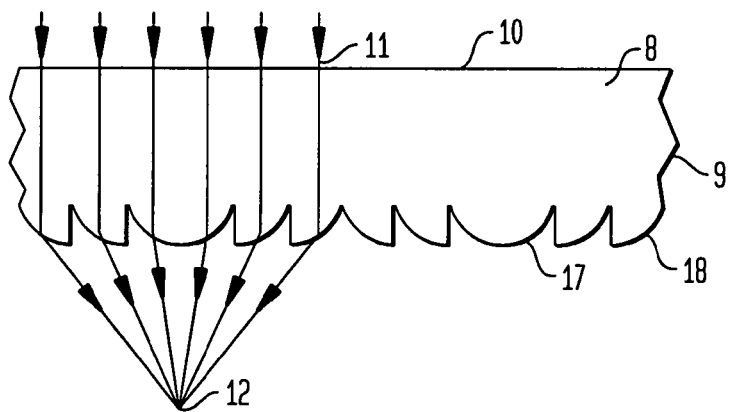

FIGS. 4–4C show Fresnel lens surfaces 17 and 18 formed on a refracting material 8. to Changing the profile of Fresnel lens surface 17 and 18, the relationship between the radius of center 17 and ring 18 of the Fresnel surface, makes it possible to achieve a desired quality of focusing. The arrays of FIGS. 4B and 4C permit a higher quality focusing to be achieved and are other preferred arrays. Surfaces 17 and 18 can be either spherical or aspherical.

Figure 5:
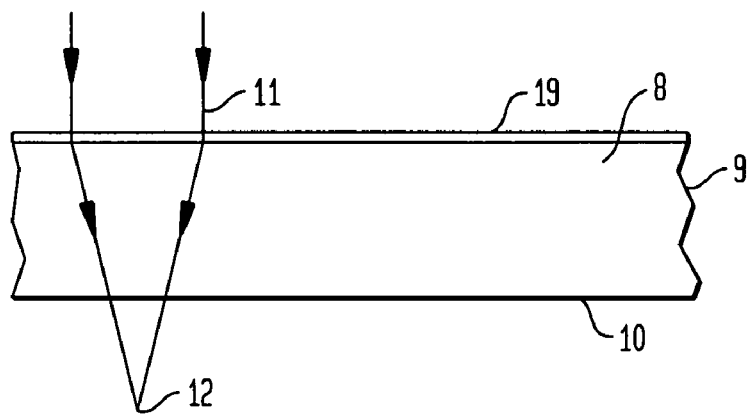
FIGS. 5–5B are side views of holographic lens arrays suitable for use in delivering radiation in parallel to a plurality of target portions.
Figure 5A:
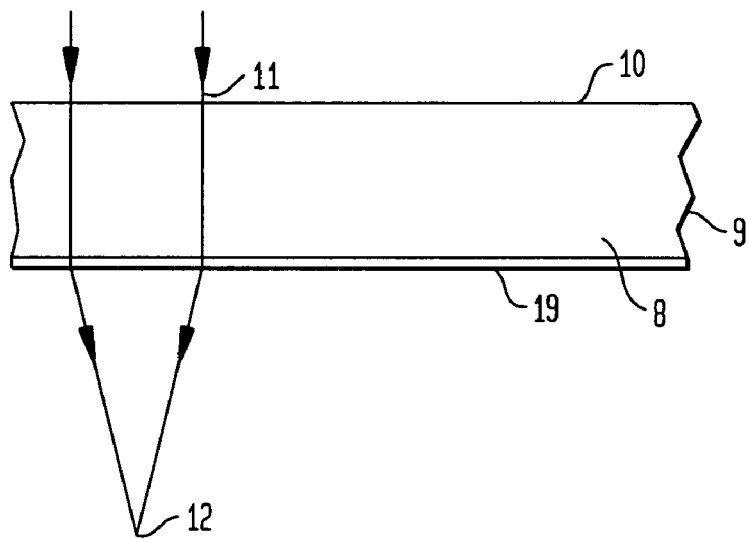
Figure 5B:
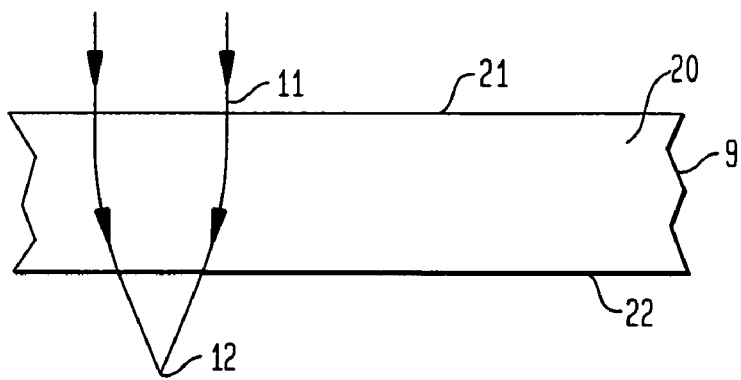

In FIGS. 5 and 5A, the focusing of an incident beam 11 is achieved by forming a holographic lens 19 (i.e., a photographic hologram) on a surface of refracting material 8. Holographic lenses 19 may be formed on either of the surfaces of refracting material 8 as shown in FIGS. 5 and 5A or on both surfaces. FIG. 5B shows that the holographic material 20 substituted for the refracting material 8 of FIGS. 5 and 5A. The holographic lens is formed in the volume of material 20.

Figure 6:
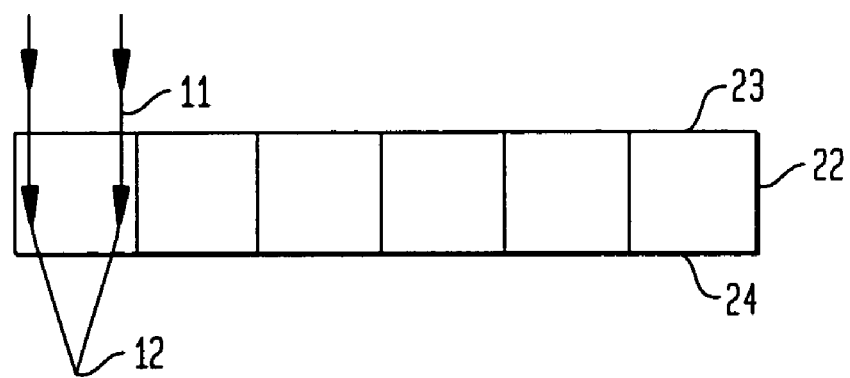
FIGS. 6–6A are side views of gradient lens arrays suitable for use in delivering radiation in parallel to a plurality of target portions.
Figure 6A:
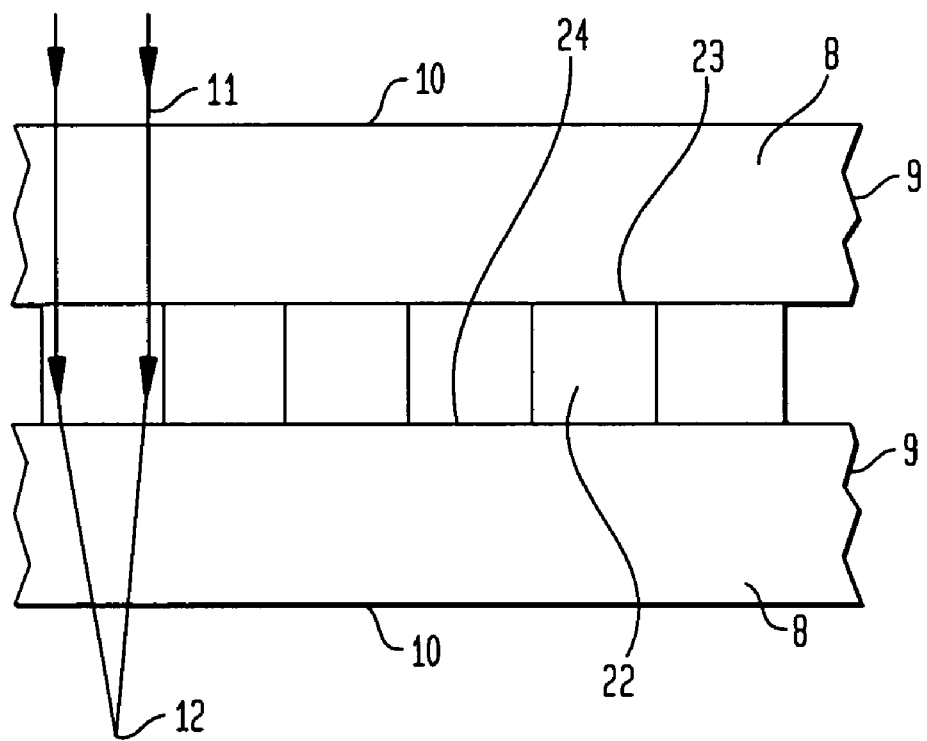

In FIGS. 6 and 6A, the focusing elements are formed by gradient lenses 22 having primary plane surfaces 23 and secondary plane surfaces 24. As shown in FIG. 6A, such gradient lenses may be sandwiched between a pair of refracting material plates 8 which provide support, protection and possibly cooling for the lenses.

Figure 7:
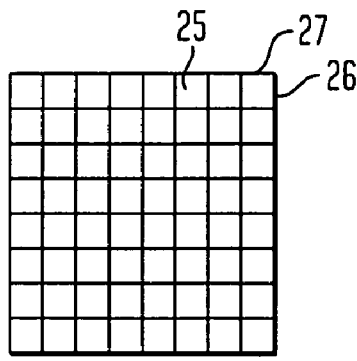
FIGS. 7–7B are top views of various matrix arrays of cylindrical lenses, some of which are suitable for providing a line focus for a plurality of target portions.
Figure 7A:
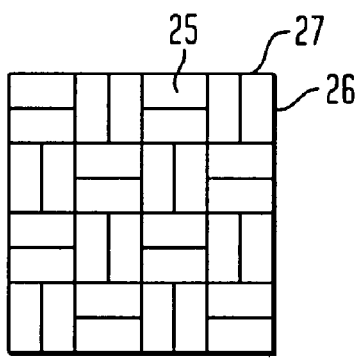
Figure 7B:
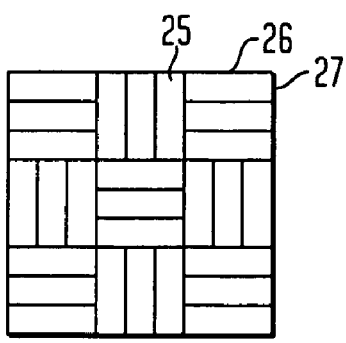

FIGS. 7, 7A and 7B illustrate various matrix arrays of cylindrical lenses 25. The relation of the lengths 26 and diameters 27 of the cylindrical lenses 25 can vary as shown in the figures. The cylindrical lens 25 of FIGS. 7A and 7B provide a line focus rather than a spot or circle focus as for the arrays previously shown.

Figure 8:
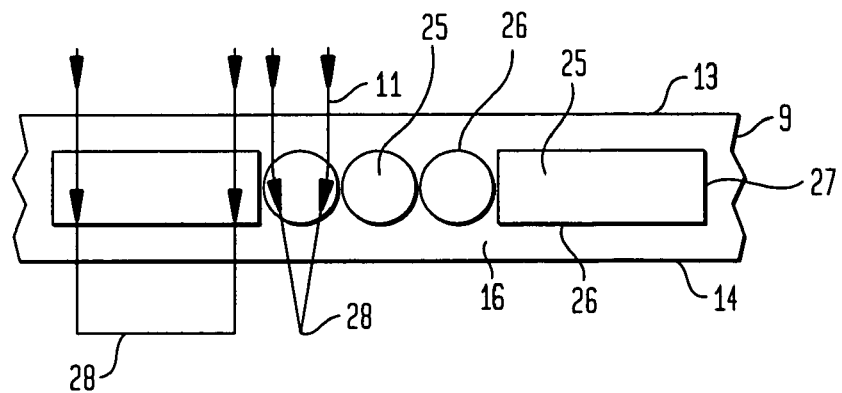
FIGS. 8–8C are cross-sectional or side views of one layer of a matrix cylindrical lens system suitable for delivering radiation in parallel to a plurality of target portions.
Figure 8A:
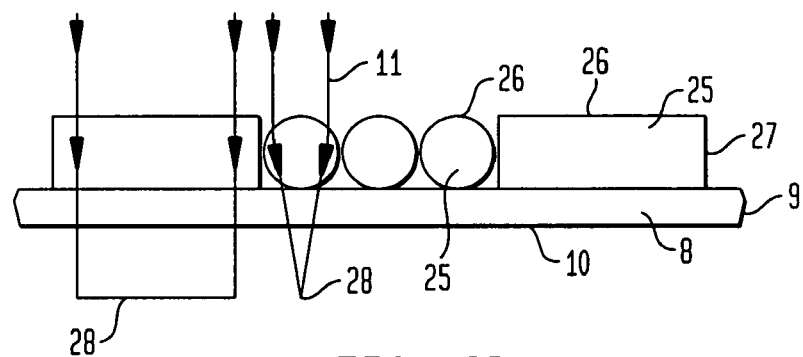
Figure 8B:
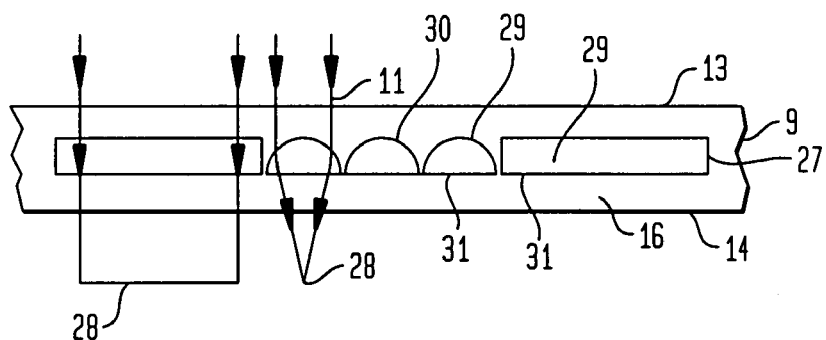
Figure 8C:
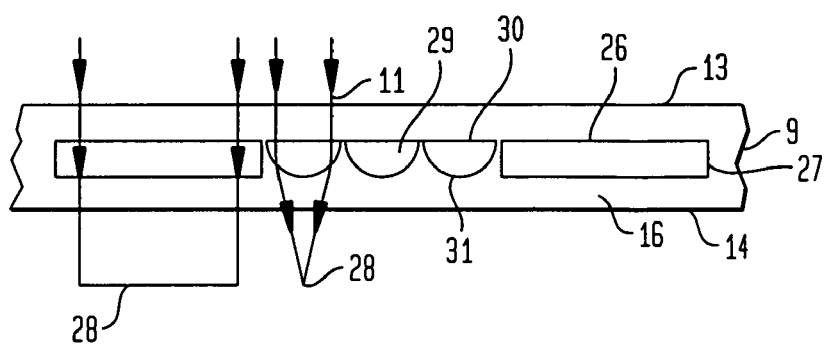

FIGS. 8–8C are cross-sectional views of one layer of a matrix cylindrical lens system. The incident beam 11 is refracted by cylindrical lenses 25 (FIGS. 8 and 8A) or half cylinder lenses 29 (FIGS. 8B and 8C) and focus to a line focus 28. In FIGS. 8B and 8C, the cylindrical lenses 29 are in the immersion material 16. Primary working optical surface 30 and secondary optical working surface 31, which may be spherical or aspherical, allowing high quality focusing to be achieved. As shown in FIGS. 7–8C the line focuses for adjacent lenses may be oriented in different directions, the orientations being at right angles to each other for certain of the lenses in these figures.

Figure 9:
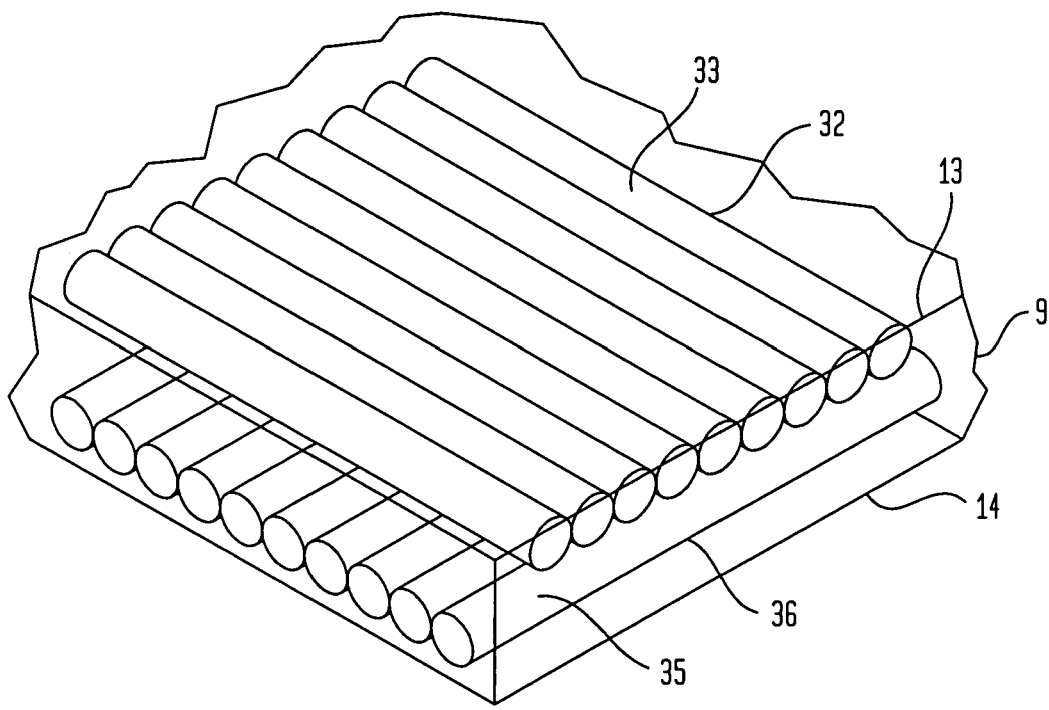
FIGS. 9–9B are a perspective view and cross-sectional side views, respectively, of a two layer cylindrical lens array suitable for delivering radiation in parallel to a plurality of target portions.
Figure 9A:
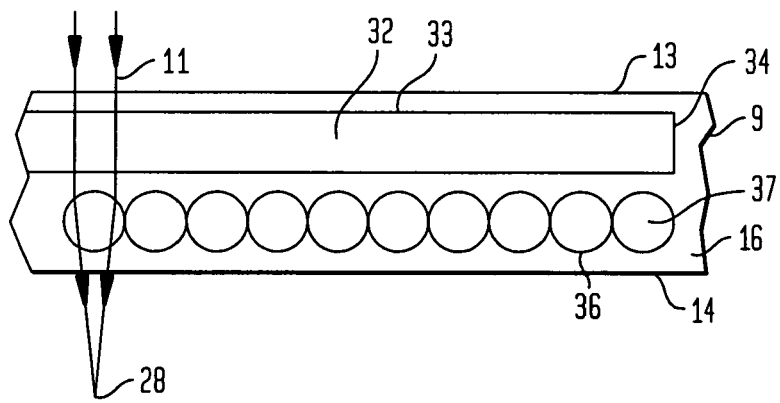
Figure 9B:
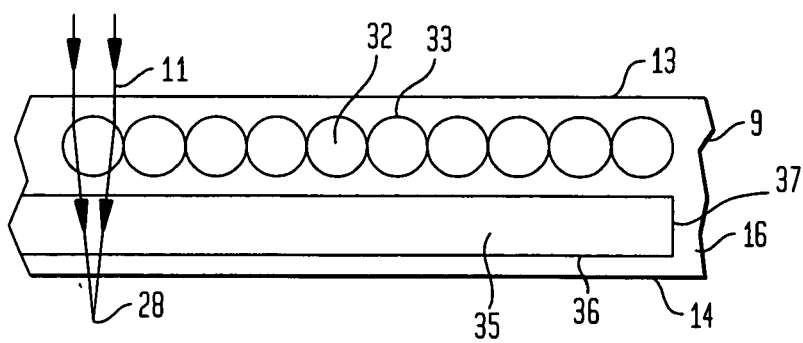

In FIGS. 9, 9A and 9B, a matrix of focal spots is achieved by passing incident beam 11 through two layers of cylindrical lenses 32 and 35. FIGS. 9A and 9B are cross-sections looking in two orthogonal directions at the array shown in FIG. 9. By changing the focal distance of primary layer lens 32, having a surface 33, and secondary lens 35, having a surface 36, it is possible to achieve a rectangular focal spot of a desired size. Primary layer lens 32 and secondary layer lens 35 are mounted in immersion material 16. Lenses 32 and 35 may be standard optical fibers or may be replaced by cylindrical lenses which may be spherical or aspherical. Surfaces 34 and 37 can be of optical quality to minimize edge losses.

Figure 10:
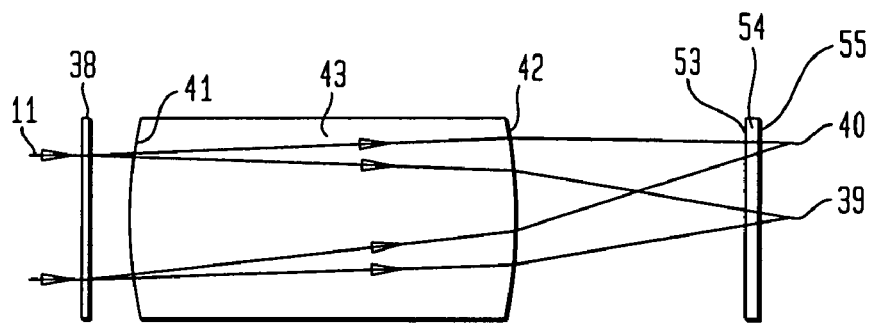
FIGS. 10–13 are side views of various optical objective arrays suitable for use in concentrating radiation to one or more target portions.

FIG. 10 shows a one lens objective 43 with a beam splitter 38. The beam 11 incident on angle beam splitter 38 divides and then passes through the refracting surfaces 41 and 42 of lens 43 to focus at central point 39 and off-center point 40. Surfaces 41 and 42 can be spherical and/or aspherical. Plate 54 having optical planar surfaces 53 and 55 permits a fixed distance to be achieved between optical surface 55 and focusing points 39, 40. Angle beam splitter 38 can act as an optical grating that can split beam 11 into several beams and provide several focuses.

Figure 11:
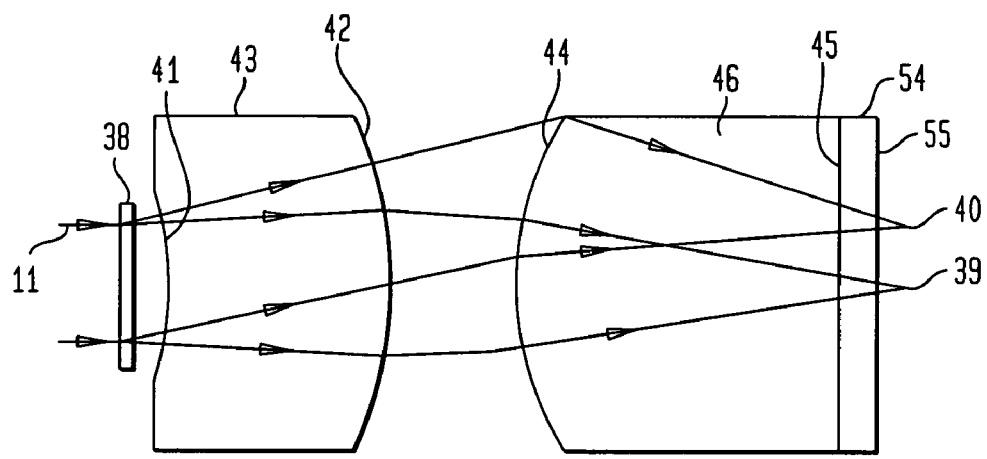

In FIG. 11, a two lens 43,46 objective provides higher quality focusing and numerical aperture as a result of optimal positioning of optical surfaces 41, 42 and 44. All of these surfaces can be spherical or aspherical. Optical surface 45 of lens 46 can be planar to increase numerical aperture and can be in contact with plate 54. Plate 54 can also be a cooling element as previously discussed.

Figure 12:
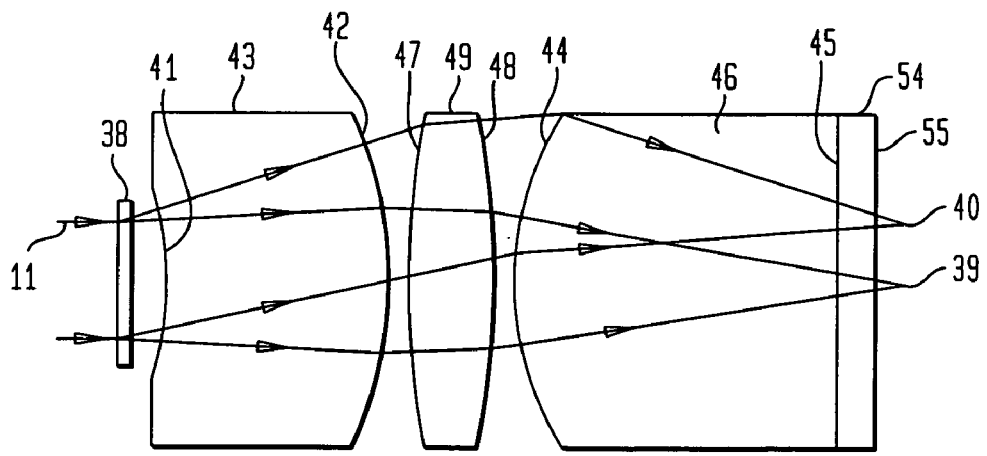
Figure 13:
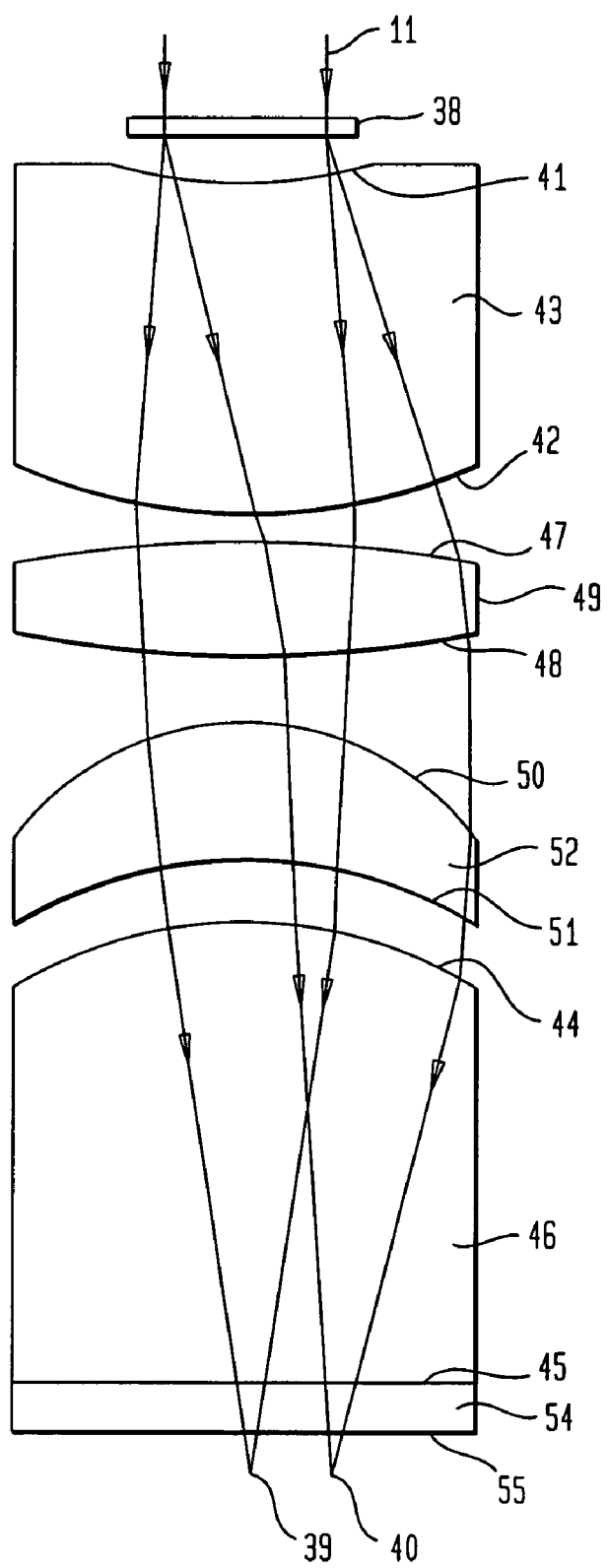

FIG. 12 differs from the previous figures in providing a three lens objective, lenses 43, 46 and 49. FIG. 13 shows a four lens objective system, the optical surfaces 50 and 51 of lens 52 allowing an increased radius of treatment area (i.e., the distance between points 39 and 40).

Figure 14:
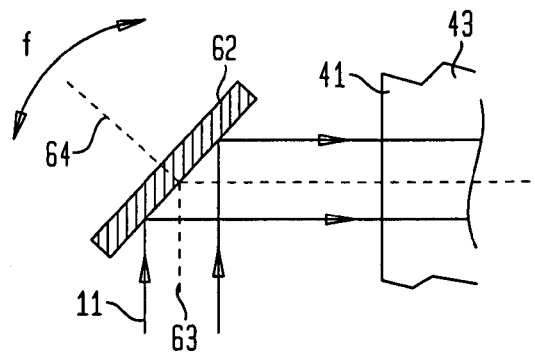
FIGS. 14–19 are side views of various deflector systems suitable for use with the arrays of FIGS. 10–13 to move to successive target portions.
Figure 14A:
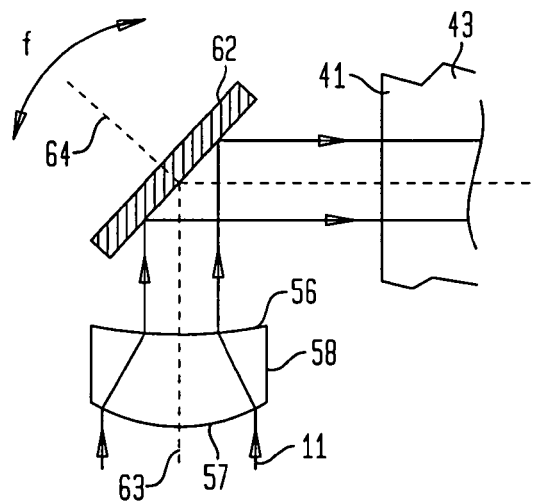
Figure 14B:
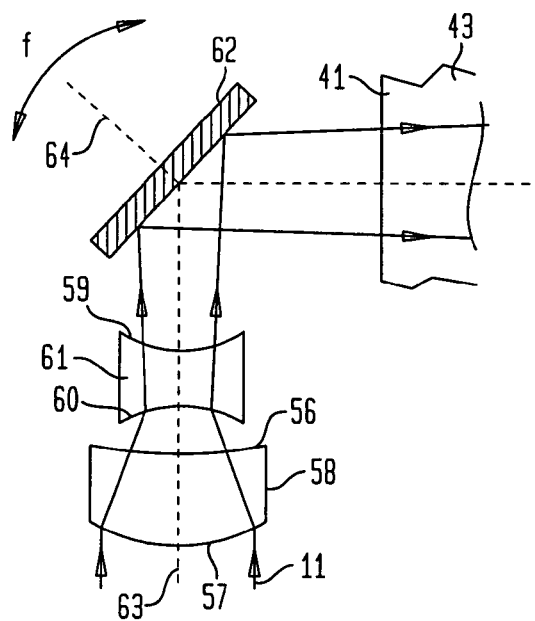

FIGS. 14, 14A and 14B illustrate three optical systems which may be utilized as scanning front ends to the various objectives shown in FIGS. 10–13. In these figures, the collimated initial beam 11 impinges on a scanning mirror 62 and is reflected by this mirror to surface 41 of the first lens 43 of the objective optics. Scanning mirror 62 is designed to move optical axis 63 over an angle f. Rotational displacement of a normal 64 of mirror 62 by an angle f causes the angle of beam 11 to be varied by an angle 2f. The optical position of scanning mirror 62 is in the entrance pupil of the focusing objective. To better correlate between the diameter of scanning mirror 62 and the radius of the working surface (i.e., the distance between points 39 and 40) and to increase the focusing quality, a lens 58 may be inserted before scanning mirror 62 as shown in FIG. 14A. Optical surfaces 56 and 57 of lens 58 can be spherical or aspherical. For additional aberration control, a lens 61 may be inserted between lens 58 and mirror 62, the lens 61 having optical surfaces 59 and 60.

Figure 15:
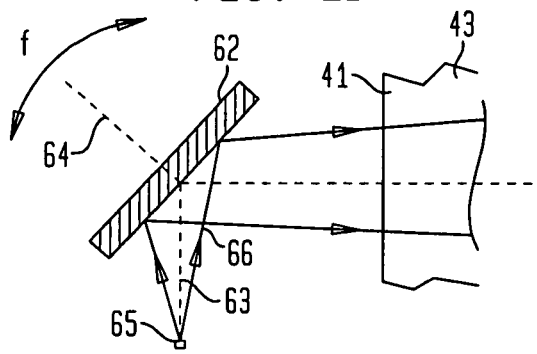
Figure 15A:
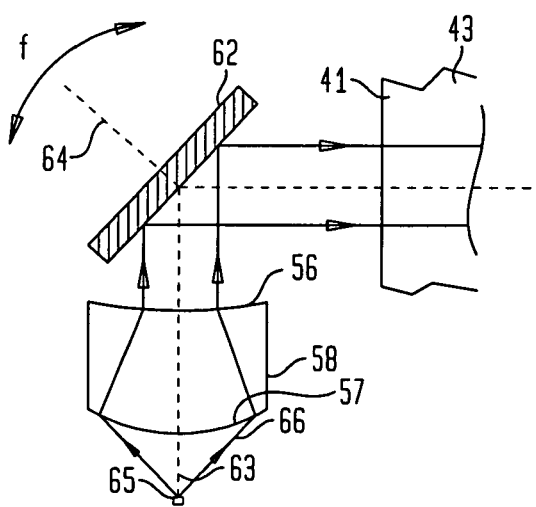
Figure 15B:
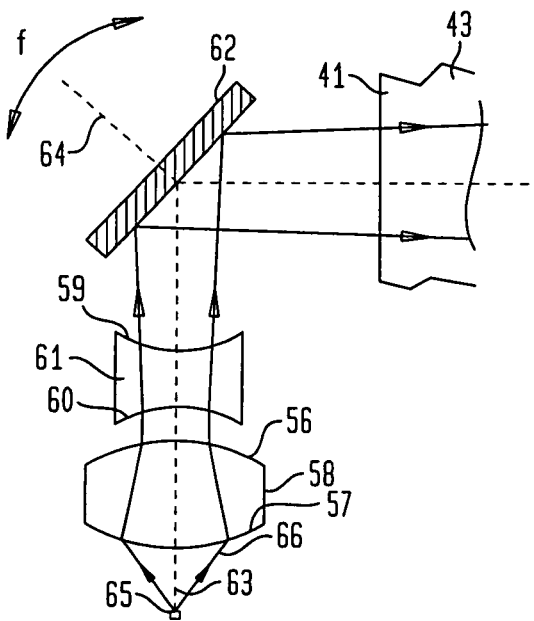

FIGS. 15, 15A and 15B are similar to FIGS. 14, 14A and 14B except that the light source is a point source or optical fiber 65 rather than collimated beam 11. Beam 66 from point source 65, for example the end of a fiber, is incident on scanning mirror 62 (FIG. 15) or on surface 57 of lens 58 (FIGS. 15A, 15B).

Figure 16:
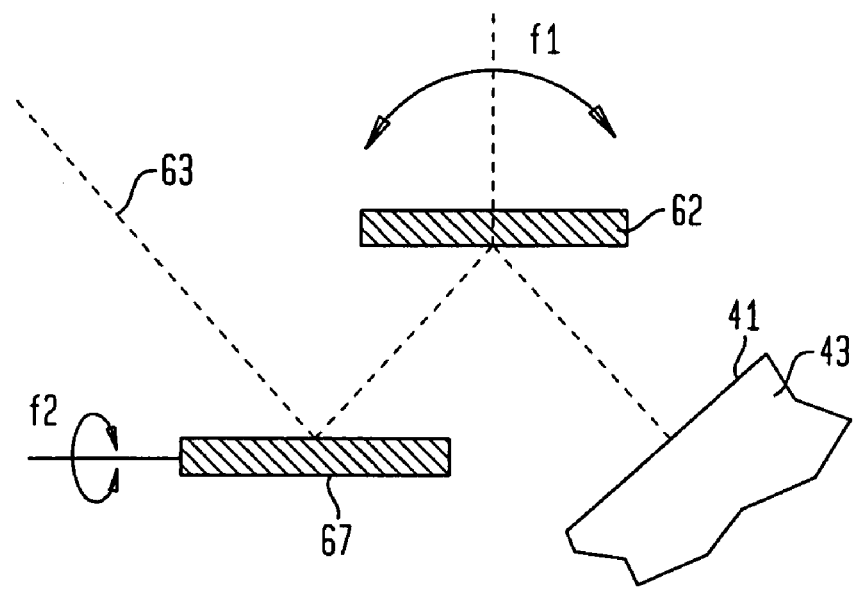
Figure 16A:
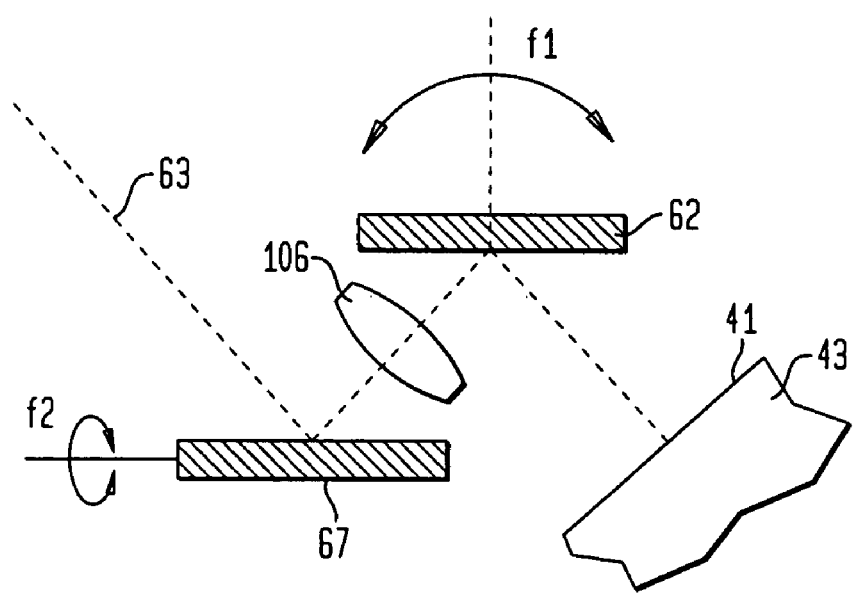

FIGS. 16 and 16A show a two mirror scanning system. In the simpler case shown in FIG. 16, scanning mirror 67 rotates over an angle f2 and scanning mirror 62 rotates over an angle f1. Beam 63 is initially incident on mirror 67 and is reflected by mirror 67 to mirror 62, from which it is reflected to surface 41 of optical lens 43. In FIG. 16A, to increase the numerical aperture of the focusing beam, increase work area on the skin and decrease aberration between scanning mirrors 62 and 67, an objective lens 106 is inserted between the mirrors. While a simple one lens objective 106 is shown in this figure, more complex objectives may be employed. Objective lens 106 refracts the beam from the center of scanning mirror 67 to the center of scanning mirror 62.

Figure 17:
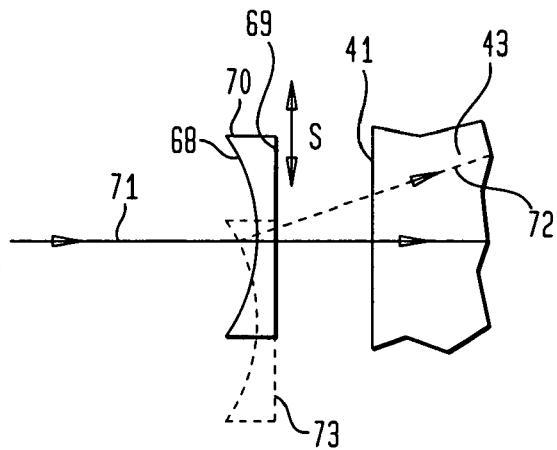

In FIG. 17, scanning is performed by scanning lens 70 which is movable in direction s. When scanning lens 70 is moved to an off center position 73, optical surface 68 refracts a ray of light along optical axis 71 to direction 72.

Figure 18:
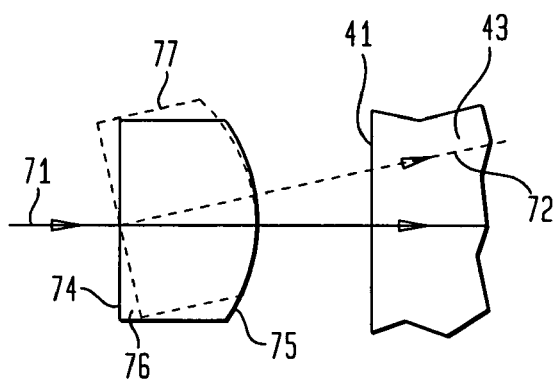

In FIG. 18, scanning is performed by rotating lens 76 to, for example, position 77. Surface 74 is planar and surface 75 is selected so that it does not influence the direction of refracted optical axis 72. In FIG. 19, scanning is performed by the moving of point source or optical fiber 65 in direction s.

FIGS. 20 and 21 show zoom lens objectives to move the island of damage to different depths. In FIG. 20, a first component is made up of a single lens 81 movable along the optical axis relative to a second component which is unmovable and consists of two lenses 84 and 87. Lens 84 is used to increase numerical aperture. To increase numerical aperture, range of back-focal distance and decrease focal spot size, optical surfaces 79, 80, 82, 83 and 85 can be aspherical. The relative position of the first and second components determines the depth of focal spot 12.

FIG. 21 shows zoom lens objectives with spherical optical surfaces. The first component is made up of a single lens 90 movable with respect to the second component along the optical axis. The second component, which is unmovable, consists of five lenses 93, 96, 99, 102, and 105. The radius of curvature of surfaces 88 and 89 are selected so as to compensate for aberrations of the unmovable second component. Again, the depth of focus may be controlled by controlling the distance between the first and second components. Either of the lens systems shown in FIGS. 20 and 21 may be mounted so as to be movable either manually or under control of control 218 to selectively focus on desired portions 214 of target volume V or to non-selectively focus on portions of the target volume.

While the invention has been shown and described above with reference to a number of embodiments, and variations on these embodiments have been discussed, these embodiments are being presented primarily for purposes of illustration and the foregoing and other changes in form and detail may be made in these embodiments by one skilled in the art without departing from the spirit and scope of the invention which is be defined only by the appended claims.

What is claimed is:

1. Apparatus for performing a therapeutic treatment on a patient's skin having a multi-focal optical system including means for concentrating applied treatment radiation of selected wavelength at a plurality of selected, three-dimensionally located, treatment portions, which treatment portions are within non-treatment portions,
    said optical system comprising a controller for successively directing said applied radiation to said treatment portions.

2. Apparatus for performing a treatment on a volume located at area and depth coordinates of a patient's skin including:
    a source of treatment radiation;
    a mechanism which cools the patient's skin over said area coordinate to a selected temperature;
    controls for selectively operating said mechanism to at least one of precool said skin for a selected duration before application of radiation and during application of radiation, said mechanism and controls cooling to a temperature and for a duration sufficient to cool said skin to at least a selected temperature below normal body temperature to at least a depth below said depth coordinate; and
    an optical system including multiple foci to which treatment radiation from said source is selectively applied, said optical system concentrating said treatment radiation to a depth in said volume and to selected areas of said volume to define treatment portions, said treatment portions being less than said total volume, each said portion being substantially surrounded by untreated and cooled skin,
    said optical system further comprising a controller for successively directing said radiation to said multiple foci.

3. Apparatus as claimed in claim 2 wherein said radiation is applied to said optical system for a duration which is greater than thermal relaxation time of each portion.

4. Apparatus for performing a treatment on a volume located at area and depth coordinates of a patient's skin including:
    a source of treatment radiation; and
    an optical system to which treatment radiation from said source is applied, said optical system providing a plurality of foci for concentrating said treatment radiation to at least one depth in said volume and to selected areas of said volume, said at least one depth and said areas defining three dimensional treatment portions in said volume within untreated portions of said volume,
    a controller for selectively activating said source so as to successively irradiate said plurality of foci.

5. Apparatus as claimed in claim 4, wherein said foci are configured such that said selected portions of said volume are one of cylinders, spheres, ellipsoids, solid rectangles and planes of a selected size and thickness spaced by a selected distance.

6. Apparatus as claimed in claim 4, wherein said foci are configured such that said selected portions of said volume are spaced lines of a selected length and thickness.

7. Apparatus as claimed in claim 4 wherein said source generates radiation at a wavelength which is neither highly absorbent nor highly scattering in at least the parts of the patient's skin above said volume.

8. Apparatus as claimed in claim 4 wherein, for deeper depth coordinates, said optical system concentrates to a selected depth below said at least one depth in order to achieve concentration at said depth in the patient's skin.

9. Apparatus as claimed in claim 4 including a detector for at least one selected condition in at least one of said volume and a part of patient's skin above said volume, said optical system operating in response to said detector to control the treatment portions of said volume to which said radiation is concentrated.

10. Apparatus as claimed in claim 4 including a mechanism which cools the part of the patient's skin at least over said selected area coordinate to a selected temperature, and controls for selectively operating said mechanism to at least one of precool said part of the patient's skin for a selected duration before application of radiation and during application of radiation.

11. Apparatus as claimed in claim 10 wherein said skin is cooled to at least said selected temperature to a depth below said at least one depth, whereby each said treatment portion is substantially surrounded by cooled skin.

12. Apparatus as claimed in claim 4 wherein said optical system includes adjustable depth optical focusing components, and a positioning mechanism for said optical focusing components which moves the component to focus at successive treatment portions.

13. Apparatus as claimed in claim 12 wherein said mechanism and controls precool said skin to a temperature and for a duration sufficient to cool the part of the skin to at least a selected temperature below normal body temperature to at least said at least one depth.

14. Apparatus as claimed in claim 4 wherein said optical system includes an array of optical elements to at least a plurality of which radiation from said source is applied, each said optical element concentrating said radiation to a selected treatment portion of said volume.

15. Apparatus as claimed in claim 14 wherein each of said optical elements focuses to a line of selected length and thickness, the lines for some of said elements being at a selected angle to the lines for other of said elements.

16. Apparatus as claimed in claim 14, wherein said optical system includes apparatus for scanning radiation applied to said optical elements so as to successively focus said radiation to N of said treatment portions at a time, where $N \geq 1$.

17. Apparatus as claimed in claim 4, wherein said foci are separated such that the ratio of said treatment portions to said volume is between about 0.1% and about 90%.

18. Apparatus as claimed in claim 17, wherein said foci are separated such that said ratio is about 10% to about 50%.

19. Apparatus as claimed in claim 18, wherein said foci are separated such that said ratio is about 10% to about 30%.

20. A method for performing a therapeutic treatment on a patient's skin by utilizing a multi-focal optical system to concentrate applied treatment radiation of selected wavelength at a plurality of selected, three-dimensionally located, treatment portions such that following application of the treatment radiation the treatment portions are separated from one another by non-treatment portions.

21. A method of treating a volume of a patient's skin by irradiating portions of the volume, comprising:
    irradiating by treatment radiation a plurality of spatially separated three-dimensional portions within a volume of the skin requiring treatment for a dermatological condition such that following application of the treatment radiation each irradiated portion is surrounded by a non-irradiated portion, wherein said irradiated portions comprise a fraction of said volume in a range of about 10% to about 30%.

22. A method of treating a volume of a patient's skin by irradiating portions of the volume, comprising
    providing a source of treatment radiation,
    directing treatment radiation from said source to a plurality of spatially separated three-dimensional treatment portions disposed in a selected volume of the patient's tissue requiring treatment such that different treatment portions are irradiated sequentially over time such that following application of the treatment radiation each treatment portion is surrounded by an untreated portion of said volume,
    wherein said treatment portions comprise a fraction of said volume ranging from about 10% to about 50%.

23. The method of claim 22, wherein said step of directing radiation comprises illuminating in a temporal sequence different portions of an optical system which directs radiation to said different treatment portions.

24. A method of treating a selected volume of a patient's skin by irradiating portions of the volume, comprising:
    providing a source for generating treatment radiation, and focusing said treatment radiation sequentially over time onto selected treatment regions within said volume such that following application of the treatment radiation each treatment region is separated from other treatment regions by untreated tissue within said volume.

25. The method of claim 24, wherein said temporally sequential focusing comprises successively focusing said radiation onto a single treatment region at a time.

26. The method of claim 24, wherein said temporally sequential focusing comprises successively focusing said radiation onto a plurality of treatment regions at a time.

27. The method of claim 24, wherein said treatment regions comprise a fraction of said selected volume in a range of about 1 percent to about 50 percent.

28. The method of claim 24, wherein said treatment regions comprise a fraction of said selected volume in a range of about 10 percent to about 30 percent.

29. A method for performing a treatment on a volume located at area and depth coordinates of a patient's skin by irradiating portions of the volume including:
    providing a source of treatment radiation; and
    applying treatment radiation from said source to an optical system providing multiple foci for concentrating said radiation to at least one depth within said depth coordinate and to selected areas within said area coordinates of said volume such that following application of the treatment radiation three dimensionally located treatment portions are formed in said volume separated from one another by untreated portions of said volume.

30. A method as claimed in claim 29 wherein said treatment portions are one of cylinders, spheres, ellipsoids, solid rectangles or planes of at least one selected size and thickness.

31. A method as claimed in claim 29 wherein said treatment portions are spaced lines of a selected length and thickness.

32. A method as claimed in claim 29 wherein said optical system applies said radiation to all said treatment portions substantially simultaneously.

33. A method as claimed in claim 29 wherein said optical system applies said radiation to at least said treatment portions sequentially.

34. A method as claimed in claim 29 wherein wavelength for said radiation source is selected so as not to be either highly absorbed or scattered in the patient's skin above said volume.

35. A method as claimed in claim 29 wherein, for deeper depth coordinates, said optical system focuses radiation to a selected depth below said at least one depth in order to achieve concentration at said depth coordinate in the patient's skin.

36. A method as claimed in claim 29 including detecting selected conditions in at least one of said volume and the patient's skin above said volume, and utilizing results of said detecting during said applying step to control the treatment portions to which said radiation is concentrated.

37. A method as claimed in claim 29 wherein a vascular lesion at a selected depth is being treated, treatment parameters, including the optical system and the wavelength of the applied radiation, being selected so that said at least one depth is a depth of the vessel being treated.

38. A method as claimed in claim 29 wherein the treatment is skin remodulation, by treatment of collagen, treatment parameters, including optical system and the wavelength of applied radiation, being selected so that said at least one depth is at a depth of interdermal collagen.

39. A method as claimed in claim 29 wherein the treatment is hair removal, the treatment parameters, including optical system and the wavelength of the applied radiation, being selected so that said at least one depth is at a depth of at least one of bulge and matrix of each hair follicle.

40. A method as claimed in claim 29 wherein the treatment is removal of one of tattoos and pigmented lesions, said treatment portions being within the tattoo/pigmented lesion being treated, at least two treatments, each with a selected treatment portion pattern being performed.

41. A method as claimed in claim 29 wherein the treatment comprises treatment of acne by damage to sebaceous glands, treatment of intradermal parasites, and treatment of various skin blemishes.

42. The method of claim 29, wherein said optical system provides said multiple foci substantially simultaneously.

43. The method of claim 29, wherein said optical system provides said multiple foci temporally separately.

44. A method as claimed in claim 29 wherein the ratio of said treatment portions to said volume is between 0.1% and 90%.

45. A method as claimed in claim 44 wherein said ratio is 10% to 50%.

46. A method as claimed in claim 44 wherein said ratio is 10% to 30%.

47. A method as claimed in claim 29 wherein said radiation source has an output the wavelength of which is at least in part a function of said at least one depth.

48. A method as claimed in claim 47, further comprising selecting a wavelength of the applied radiation as a function of said at least one depth as follows:
  depth=0.5 to 0.2 mm, wavelength=400–1880 nm & 2050–2350 nm;
  depth=0.2 to 0.3 mm, wavelength=500–1880 nm & 2050–2350 nm;
  depth=0.3 to 0.5 mm, wavelength=600–1380 nm & 1520–1850 nm & 2150–2260 nm;
  depth=0.5 to 1.0 mm, wavelength=600–1370 nm & 1600–1820 nm;
  depth=1.0 to 2.0mm, wavelength=670–1350 nm & 1650–1780 nm; and
  depth=2.0 to 5.0 mm, wavelength=800–1300 nm.

49. A method as claimed in claim 47, further comprising selecting a wavelength of the applied radiation as a function of said at least one depth as follows:
  depth=0.5 to 0.2 mm, wavelength=800–1850 nm & 2100–2300 nm;
  depth=0.2 to 0.3 mm, wavelength=800–1850 nm & 2150–2300 nm;
  depth=0.3 to 0.5 mm, wavelength=900–1300 nm & 1550–1820 nm & 2150–2250 nm;
  depth=0.5 to 1.0 mm, wavelength=900–1250 nm & 1650–1750 nm;
  depth=1.0 to 2.0 mm, wavelength=900–1230 nm; and
  depth=2.0 to 5.0 mm, wavelength=1050–1220 nm.

50. A method as claimed in claim 29 including precooling the patient's skin over said treatment portions to a selected temperature for a selected duration.

51. A method as claimed in claim 50 wherein said selected temperature and duration for said precooling step are sufficient to cool said skin to at least a selected temperature below normal body temperature to at least said at least one depth.

52. A method as claimed in claim 51 wherein said skin is cooled to at least said selected temperature to a depth below said at least one depth, whereby said treatment portions are substantially surrounded by cooled skin.

53. A method as claimed in claim 52 including continuing to cool the patient's skin during said applying radiation step.

54. A method as claimed in claim 52 wherein the duration of said applying step is greater than the thermal relaxation time of treatment portions.

55. A method for performing a treatment on a volume located at area and depth coordinates of a patient's skin by irradiating portions of the volume including:
  providing a source of treatment radiation;
  precooling the patient's skin over at least part of said area coordinate to selected temperature for a selected duration, said selected temperature and duration being sufficient to cool said skin to a depth below said depth coordinate to a temperature below normal body temperature, and
  applying said treatment radiation to an optical system having a plurality of foci which concentrates said radiation to at least one depth coordinate and to selected areas within said area coordinate to define treatment portions in said volume following application of the treatment radiation, said treatment portions being less than said volume, each said treatment portion being within untreated portions and being substantially surrounded by cooled skin separating said treatment portion from other treatment portions.

56. A method as claimed in claim 55 including continuing to cool the patient's skin during said applying step.

57. A method as claimed in claim 55 wherein the duration of said applying step is greater than the thermal relaxation time of each treatment portion.

* * * * *